(12) United States Patent
Allendorf et al.

(10) Patent No.: US 9,718,748 B1
(45) Date of Patent: Aug. 1, 2017

(54) METAL-ORGANIC FRAMEWORK CATALYSTS FOR SELECTIVE CLEAVAGE OF ARYL-ETHER BONDS

(71) Applicant: Sandia Corporation, Albuquerque, NM (US)

(72) Inventors: Mark D. Allendorf, Pleasanton, CA (US); Vitalie Stavila, Pleasanton, CA (US)

(73) Assignee: Sandia Corporation, Albuquerque, NM (US)

( * ) Notice: Subject to any disclaimer, the term of this patent is extended or adjusted under 35 U.S.C. 154(b) by 192 days.

(21) Appl. No.: 14/991,734

(22) Filed: Jan. 8, 2016

Related U.S. Application Data

(60) Provisional application No. 62/101,303, filed on Jan. 8, 2015.

(51) Int. Cl.
| | | |
|---|---|---|
| C07C 37/00 | (2006.01) |
| C07C 1/00 | (2006.01) |
| C07C 29/132 | (2006.01) |
| B01J 31/16 | (2006.01) |
| C07C 1/22 | (2006.01) |

(52) U.S. Cl.
CPC ......... *C07C 29/132* (2013.01); *B01J 31/1691* (2013.01); *C07C 1/22* (2013.01); *C07C 2531/20* (2013.01); *C07C 2531/22* (2013.01)

(58) Field of Classification Search
CPC ..... C07C 37/055; C07C 37/54; B01J 31/1691
USPC .......................................... 568/799; 585/476
See application file for complete search history.

(56) References Cited

U.S. PATENT DOCUMENTS

| | | |
|---|---|---|
| 7,027,150 B1 | 4/2006 | Rice et al. |
| 7,985,868 B1 | 7/2011 | Bauer et al. |
| 8,065,904 B1 | 11/2011 | Allendorf et al. |
| 8,853,651 B2 | 10/2014 | Doty et al. |
| 8,904,850 B1 | 12/2014 | Allendorf et al. |
| 2011/0108738 A1 | 5/2011 | Doty et al. |

OTHER PUBLICATIONS

U.S. Appl. No. 13/633,772, filed Oct. 2, 2012, Allendorf et al.
U.S. Appl. No. 14/469,459, filed Aug. 26, 2014, Talin et al.
U.S. Appl. No. 14/573,990, filed Dec. 17, 2014, Talin et al.
U.S. Appl. No. 14/591,550, filed Jan. 7, 2015, Allendorf et al.
U.S. Appl. No. 14/595,034, filed Jan. 12, 2015, Allendorf et al.
U.S. Appl. No. 14/662,098, filed Mar. 18, 2015, Allendorf et al.
U.S. Appl. No. 14/957,397, filed Dec. 2, 2015, Feng et al.
U.S. Appl. No. 14/957,401, filed Dec. 2, 2015, Doty et al.
Aijaz A et al., "Catalysis with metal nanoparticles immobilized within the pores of metal-organic frameworks," *J. Phys. Chem. Lett.* 2014;5:1400-11.
Allendorf MD et al., "Bio-inspired MOF-based catalysts for lignin valorization," *Sandia Report* No. SAND2014-18259, 2014 (27 pp.).
Barta K et al., "Catalytic conversion of nonfood woody biomass solids to organic liquids," *Acc. Chem. Res.* 2014;47(5):1503-12.
Biesinger MC et al., "Resolving surface chemical states in XPS analysis of first row transition metals, oxides and hydroxides: Cr, Mn, Fe, Co and Ni," *Appl. Surf. Sci.* 2011;257(7):2717-30.
Biesinger MC et al., "The role of the Auger parameter in XPS studies of nickel metal, halides and oxides," *Phys. Chem. Chem. Phys.* 2012;14:2434-42.
Boys SF et al., "The calculation of small molecular interactions by the differences of separate total energies: some procedures with reduced errors," *Mol. Phys.* 1970;19(4):553-66.
Burtch NC et al., "Water stability and adsorption in metal-organic frameworks," *Chem. Rev.* 2014;114:10575-612.
Caskey SR et al., "Dramatic tuning of carbon dioxide uptake via metal substitution in a coordination polymer with cylindrical pores," *J. Am Chem. Soc.* 2008; 130(33):10870-1.
Colombo V et al., "High thermal and chemical stability in pyrazolate-bridged metal-organic frameworks with exposed metal sites," *Chem. Sci.* 2011;2:1311-9.
Corma A et al., "Engineering metal organic frameworks for heterogeneous catalysis," *Chem. Rev.* 2010;110:4606-55.
Deng H et al., "Large-pore apertures in a series of metal-organic frameworks," *Science* 2012;336(6084):1018-23.
Furukawa H et al., "The chemistry and applications of metal-organic frameworks," *Science* 2013;341(6149):1230444 (13 pp.)).
Gascon J et al., "Metal organic framework catalysis: quo vadis?," *ACS Catal.* 2014;4:361-78.
Guo Z et al., "Pt nanoclusters confined within metal-organic framework cavities for chemoselective cinnamaldehyde hydrogenation," *ACS Catal.* 2014;4:1340-8.
He J et al., "Ni-catalyzed cleavage of aryl ethers in the aqueous phase," *J. Am. Chem. Soc.* 2012;134:20768-75.
Higman C et al., "Advances in coal gasification, hydrogenation, and gas treating for the production of chemicals and fuels," *Chem. Rev.* 2014;114(3):1673-708.
Horcajada P et al., "Metal—organic frameworks in biomedicine," *Chem. Rev.* 2012;112:1232-68.
Kreno E et al., "Metal-organic framework materials as chemical sensors," *Chem. Rev.* 2012;112:1105-25.
Lee J et al., "Metal-organic framework materials as catalysts," *Chem. Soc. Rev.* 2009;38:1450-9.
Lee K et al., "Small-molecule adsorption in open-site metal-organic frameworks: a systematic density functional theory study for rational design," *Chem. Mater.* 2015;27:668-78.
Li JR et al., "Selective gas adsorption and separation in metal-organic frameworks," *Chem. Soc. Rev.* 2009;38:1477-504.
Liu J et al., "Applications of metal-organic frameworks in heterogeneous supramolecular catalysis," *Chem. Soc. Rev.* 2014;43:6011-61.
Meilikhov M et al., "Metals@MOFs—loading MOFs with metal nanoparticles for hybrid functions," *Eur. J. Inorg. Chem.* 2010;24:3701-14.

(Continued)

*Primary Examiner* — Sikarl Witherspoon
(74) *Attorney, Agent, or Firm* — Helen S. Baca

(57) ABSTRACT

The present invention relates to methods of employing a metal-organic framework (MOF) as a catalyst for cleaving chemical bonds. In particular instances, the MOF results in selective bond cleavage that results in hydrogenolyzis. Furthermore, the MOF catalyst can be reused in multiple cycles. Such MOF-based catalysts can be useful, e.g., to convert biomass components.

19 Claims, 12 Drawing Sheets

(56) References Cited

OTHER PUBLICATIONS

Molinari V et al., "Titanium nitride-nickel nanocomposite as heterogeneous catalyst for the hydrogenolysis of aryl ethers," *J. Am. Chem. Soc.* 2014;136(5):1758-61.

Mousty-Desbuquoit C et al., "Electronic structure of titanium(III) and titanium(IV) halides studied by solid-phase x-ray photoelectron spectroscopy," *Inorg. Chem.* 1987;26(8):1212-7.

Nanayakkara S et al., "Chemical depolymerization of lignin involving the redistribution mechanism with phenols and repolymerization of depolymerized products," *Green Chem.* 2014;16:1897-903.

Park YK et al., "Catalytic nickel nanoparticles embedded in a mesoporous metal-organic framework," *Chem. Commun.* 2010;46:3086-88.

Parr RG et al., "Absolute hardness: companion parameter to absolute electronegativity," *J. Am. Chem. Soc.* 1983;105(26):7512-6.

Perry JJ et al., "Noble gas adsorption in metal-organic frameworks containing open metal sites," *J. Phys. Chem. C* 2014;118(22):11685-98.

Phung X et al., "Surface characterization of metal nanoparticles," *Mater. Sci. Eng. A* 2003;359(1-2):261-8.

Ruppert AM et al., "Hydrogenolysis goes bio: from carbohydrates and sugar alcohols to platform chemicals," *Angew. Chem. Int. Ed.* 2012;51:2564-601.

Saillard JY et al., "Carbon-hydrogen and hydrogen-hydrogen activation in transition metal complexes and on surfaces," *J. Am. Chem. Soc.* 1984;106(7):2006-26.

Sanderson RT, "An interpretation of bond lengths and a classification of bonds," *Science* 1951;114(2973):670-2.

Sergeev AG et al., "A heterogeneous nickel catalyst for the hydrogenolysis of aryl ethers without arene hydrogenation," *J. Am. Chem. Soc.* 2012;134(50):20226-9.

Sergeev AG et al., "Selective, nickel-catalyzed hydrogenolysis of aryl ethers," *Science* 2011;332:439-43.

Stavila V et al., "MOF-based catalysts for selective hydrogenolysis of carbon-oxygen ether bonds," *ACS Catal.* 2016;6:55-9.

Stavila V et al., Supporting Information for "MOF-based catalysts for selective hydrogenolysis of carbon—oxygen ether bonds," *ACS Catal.* 2016;6:55-9 (18 pp.).

Stavila V et al., "Reversible hydrogen storage by $NaAlH_4$ . confined within a titanium-functionalized MOF-74(Mg) nanoreactor," *ACS Nano* 2012;6(11):9807-17.

Stavila V et al., Supporting Information for "Reversible hydrogen storage by $NaAlH_4$ . confined within a titanium-functionalized MOF-74(Mg) nanoreactor," *ACS Nano* 2012;6(11):9807-17 (8 pp.).

Suh MP et al., "Hydrogen storage in metal-organic frameworks," *Chem. Rev.* 2012;112:782-835.

Sumida K et al., "Carbon dioxide capture in metal-organic frameworks," *Chem. Rev.* 2012;112(2):724-81.

Sumida K et al., "Hydrogen storage properties and neutron scattering studies of $Mg_2$.(dobdc)—a metal-organic framework with open $Mg^{2+}$. adsorption sites," *Chem. Commun.* 2011;47:1157-9.

Tadesse H et al., "Advances on biomass pretreatment using ionic liquids: an overview," *Energy Environ. Sci.* 2011;4:3913-29.

Wan Y et al., "Ni/MIL-120: An efficient metal-organic framework catalyst for hydrogenation of benzene to cyclohexane," *Microporous Mesoporous Mater.* 2013;171:9-13.

Wang DS et al., "Asymmetric hydrogenation of heteroarenes and arenes," *Chem. Rev.* 2012;112(4):2557-90.

Wang LJ et al., "Synthesis and characterization of metal-organic framework-74 containing 2, 4, 6, 8, and 10 different metals," *Inorg. Chem.* 2014;53:5881-3.

Wang LJ et al., Supporting Information for "Synthesis and characterization of metal-organic framework-74 containing 2, 4, 6, 8, and 10 different metals," *Inorg. Chem.* 2014;53:5881-3 (27 pp.).

Wang X et al., "Solvent effects on the hydrogenolysis of diphenyl ether with Raney nickel and their implications for the conversion of lignin," *ChemSusChem* 2012;5(8):1455-66.

Yang L et al., "Hydrolytic cleavage of C—O linkages in lignin model compounds catalyzed by water-tolerant Lewis acids," *Ind. Eng. Chem. Res.* 2014;53(7):2633-9.

Yu D et al., "A combined experimental and quantum chemical study of $CO_2$. adsorption in the metal-organic framework CPO-27 with different metals," *Chem. Sci.* 2013;4:3544-56.

Zakzeski J et al., "The catalytic valorization of lignin for the production of renewable chemicals," *Chem. Rev.* 2010;110(6):3552-99.

Zhang J et al., "Reductive degradation of lignin and model compounds by hydrosilanes," *ACS Sustainable Chem. Eng.* 2014;2(8):1983-91.

Zhao M et al., "Porous metal-organic frameworks for heterogeneous biomimetic catalysis," *Acc. Chem. Res.* 2014;47:1199-207.

METAL-ORGANIC FRAMEWORK CATALYSTS FOR SELECTIVE CLEAVAGE OF ARYL-ETHER BONDS

CROSS-REFERENCE TO RELATED APPLICATION

This application claims the benefit of U.S. Provisional Application No. 62/101,303, filed Jan. 8, 2015, which is hereby incorporated by reference in its entirety.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to methods of employing a metal-organic framework (MOF) as a catalyst for cleaving chemical bonds. In particular instances, the MOF results in selective bond cleavage that results in hydrogenolysis. Furthermore, the MOF catalyst can be reused in multiple cycles. Such MOF-based catalysts can be useful, e.g., to convert biomass components.

BACKGROUND OF THE INVENTION

Lignin is one of the most abundant biomass sources with potential to become a sustainable source of value-added chemicals and fuels. However, this goal remains challenging because of the recalcitrance and diverse structure of polymeric lignin with multiple C—O ether and carbon-carbon linkages characterized by high energies and chemical inertness.

Conventional techniques for processing lignin are energy-intensive and produce complex mixtures. Additional methods and materials are needed to provide more efficient and effective ways to degrade lignin into useful intermediates, building blocks, and fuels.

SUMMARY OF THE INVENTION

The present invention relates to methods for cleaving bonds by employing a metal-organic framework (MOF). In some embodiments, bond scission proceeds in a selective manner, such that selective bond scission is preferentially promoted and that non-specific hydrogenation is reduced. For instance, lignin includes aryl group and multiple ether bonds, and the methods herein can be employed to selectively cleave ether bonds while avoiding hydrogenation of aryl groups (e.g., avoiding the hydrogenation of phenyl groups into cyclohexyl groups).

Accordingly, in a first aspect, the present invention features a method of cleaving a bond in a test compound. In one embodiment, the method includes exposing the test compound to a metal-organic framework in the presence of a hydrogen source, thereby cleaving the bond. In some embodiments, the test compound includes a carbon-oxygen bond (e.g., an ether bond, such as an aryl ether bond), and the method results in cleaving the carbon-oxygen bond.

In some embodiments, the method includes reuse of the MOF. For instance, in some embodiments, the method includes separating the MOF from the reacted test compound; and reusing the MOF for a further reaction with another test compound.

In some embodiments, the method includes conducting a step of a reaction (e.g., an exposing step) in the presence of an ionic liquid (e.g., any described herein).

In some embodiments, the method includes conducting a step of a reaction or the entire reaction without the presence of a base (e.g., a sacrificial base).

In a second aspect, the present invention features a method including: providing a biomass component; and exposing the biomass component to a MOF. In some embodiments, the exposing step is conducted in the presence of a hydrogen source (e.g., a source including $H_2$ or a hydride (e.g., $NaBH_4$, $NaH$, $LiH$, $NaAlH_4$, $NH_3BH_3$, or $NH_3B_3H_7$)). In other embodiments, the biomass component includes a carbon-oxygen bond, and the method results in cleaving the carbon-oxygen bond present in the biomass component.

In some embodiments, the method includes conducting a step of a reaction (e.g., an exposing step) in the presence of an ionic liquid (e.g., any described herein).

In some embodiments, the method includes conducting a step of a reaction or the entire reaction without the presence of a base (e.g., a sacrificial base).

In another aspect, the invention features a method including exposing the test compound having the bond to a metal-organic framework. In some embodiments, the metal-organic framework includes one or more open metal sites. In other embodiments, the method thereby cleaves the bond in the test compound and forming two or more resultant cleavage products.

In yet another aspect, the invention features a method including: providing a biomass component; and exposing the biomass component to a metal-organic framework. In some embodiments, the metal-organic framework includes one or more open metal sites. In other embodiments, the method thereby reacts with a bond present in the biomass component.

In any embodiment herein, the metal-organic framework (MOF) includes a plurality of nodes and an organic linker connecting at least two of the plurality of nodes. In particular embodiments, at least one node includes one or more atoms (e.g., metal atoms, including metal ions). In other embodiments, each node includes a metal cluster, in which the cluster includes a plurality of metal atoms.

In any embodiment herein, at least one of the plurality of nodes includes one or more open metal sites (e.g., at least one node includes an atom that includes one or more open metal sites; or at least one node includes a plurality of atoms, in which at least one in the plurality of atoms includes one or more open metal sites).

In any embodiment herein, the MOF can include any useful metal (e.g., including a first metal), such as one or more nodes including that metal. Optionally, the MOF can include a dopant (e.g., including a second metal). In some embodiments, the MOF includes a dopant. In particular embodiments, the dopant includes a nanoparticle (e.g., disposed within a pore of the MOF). Exemplary first and second metals include any metal described herein, such as magnesium, calcium, strontium, barium, scandium, titanium, zirconium, vanadium, chromium, manganese, rhenium, iron, ruthenium, cobalt, rhodium, iridium, nickel, palladium, platinum, copper, silver, zinc, cadmium, aluminum, lead, bismuth, cerium, or a combination thereof, as well as ions thereof (e.g., cations thereof). In some embodiments, the first metal includes magnesium or an ionic form thereof. In other embodiments, the second metal includes nickel, titanium, or a combination thereof, as well as ions thereof.

In any embodiment herein, the MOF can include any useful organic linker. In some embodiments, the linker includes an optionally substituted arylene or optionally substituted heteroarylene (e.g., including one or more substituents, in which the substituent includes a functional group configured to bind to the node). Exemplary substituents and functional groups can include hydroxyl, carboxyl, carbonyl, carboxyaldehyde, amino, as well as anionic forms thereof (e.g., deprotonated forms thereof). In some embodiments, the linker includes an optionally substituted —$(C_6H_4)_n$— or optionally substituted —$(C_6H_3)_n$—, in which n is an integer between 1 and 10 (e.g., in which one or more H is substituted with one or more functional group, such as any described herein for an aryl group).

In any embodiment herein, the MOF can have any useful structural features. In one embodiment, the MOF includes one or more pores, in which at least one pore has a diameter that is at least two times larger than a dimension of the test compound.

In any embodiment herein, the test compound is an organic compound, an organic polymer, or a biomass component (e.g., lignin, cellulose, hemicellulose, and/or a fragment thereof).

In any embodiment herein, cleaving a bond (e.g., a carbon-oxygen bond) forms two or more resultant cleavage products. In some embodiments, each of the test compound and cleavage products is, independently, an organic moiety (e.g., includes one or more carbon atoms).

DEFINITIONS

As used herein, the term "about" means +/−10% of any recited value. As used herein, this term modifies any recited value, range of values, or endpoints of one or more ranges.

By "atom" is meant to include a chemical element, as well as ionic forms thereof. For example, an atom of magnesium is meant to include $Mg^0$, as well as ionic forms (e.g., cationic forms, such as $Mg^{2+}$).

By "bind" or "bond" is meant any covalent or non-covalent bonding interaction between two components. Non-covalent bonding interactions include, without limitation, hydrogen bonding, ionic interactions, halogen bonding, electrostatic interactions, π bond interactions, hydrophobic interactions, inclusion complexes, clathration, van der Waals interactions, and combinations thereof.

By "alkaryl" is meant an aryl group, as defined herein, attached to the parent molecular group through an alkylene group, as defined herein. Similarly, by the term "alkheteroaryl" is meant a heteroaryl group, as defined herein, attached to the parent molecular group through an alkylene group. Other groups preceded by the prefix "alk-" are defined in the same manner. The alkaryl group can be substituted or unsubstituted. For example, the alkaryl group can be substituted with one or more substitution groups, as described herein for alkyl and/or aryl. Exemplary unsubstituted alkaryl groups are of from 7 to 16 carbons ($C_{7-16}$ alkaryl), as well as those having an alkylene group with 1 to 6 carbons and an aryl group with 4 to 18 carbons (i.e., $C_{1-6}$ alk-$C_{4-18}$ aryl).

By "alkyl" and the prefix "alk" is meant a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic (e.g., $C_{3-24}$ cycloalkyl) or acyclic. The alkyl group can be branched or unbranched. The alkyl group can also be substituted or unsubstituted. For example, the alkyl group can be substituted with one, two, three or, in the case of alkyl groups of two carbons or more, four substituents independently selected from the group consisting of: (1) $C_{1-6}$ alkoxy (e.g., —$OR^{Ak}$, in which $R^{Ak}$ is an optionally substituted alkyl, as defined herein); (2) $C_{1-6}$ alkylsulfinyl (e.g., —$S(O)R^{Ak}$, in which $R^{Ak}$ is an optionally substituted alkyl, as defined herein); (3) $C_{1-6}$ alkylsulfonyl (e.g., —$SO_2R^{Ak}$, in which R is an optionally substituted alkyl, as defined herein); (4) amino; (5) aryl; (6) arylalkoxy (e.g., —$OR^{a1}R^{Ar}$, in which $R^{a1}$ is an optionally substituted alkylene, as defined herein, and $R^{Ar}$ is an optionally substituted aryl group, as defined herein); (7) aryloyl (e.g., —$C(O)R^{Ar}$, in which $R^{Ar}$ is an optionally substituted aryl, as defined herein); (8) azido (e.g., an $N_3$ group); (9) cyano (e.g., a —CN group); (10) carboxyaldehyde (e.g., a —C(O)H group); (11) $C_{3-8}$ cycloalkyl; (12) halo (e.g., F, Cl, Br, or I); (13) heterocyclyl; (14) heterocyclyloxy (e.g., —$OR^{Het}$, in which $R^{Het}$ is an optionally substituted heterocyclyl, as defined herein); (15) heterocyclyloyl (e.g., —$C(O)R^{Het}$, in which $R^{Het}$ is an optionally substituted heterocyclyl, as defined herein); (16) hydroxyl (e.g., an =OH group); (17) N-protected amino; (18) nitro (e.g., an —$NO_2$ group); (19) oxo (e.g., an =O group); (20) $C_{3-8}$ spirocyclyl (e.g., an alkylene diradical or a heteroalkylene diradical, both ends of which are bonded to the same carbon atom of the parent group); (21) $C_{1-6}$ thioalkoxy (e.g., —$SR^{Ak}$, in which $R^{Ak}$ is an optionally substituted alkyl, as defined herein); (22) thiol (e.g., an —SH group); (23) —$CO_2R^A$, where $R^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (24) —$C(O)NR^BR^C$, where each of $R^B$ and $R^C$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (25) —$SO_2R^D$, where $R^D$ is selected from the group consisting of (a) $C_{1-6}$ alkyl, (b) $C_{4-18}$ aryl, and (c) $C_{1-6}$ alk-$C_{4-18}$ aryl; (26) —$SO_2NR^ER^F$, where each of $R^E$ and $R^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; and (27) —$NR^GR^H$, where each of $R^G$ and $R^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group. The alkyl group can be a primary, secondary, or tertiary alkyl group substituted with one or more substituents (e.g., one or more halo or alkoxy). In some embodiments, the unsubstituted alkyl group is a $C_{1-3}$, $C_{1-6}$, $C_{1-12}$, $C_{1-16}$, $C_{1-18}$, $C_{1-20}$, or $C_{1-24}$ alkyl group.

By "alkylene" is meant a bivalent form of an alkyl group, as described herein. Exemplary alkylene groups include methylene, ethylene, propylene, butylene, etc. In some embodiments, the alkylene group is a $C_{1-3}$, $C_{1-6}$, $C_{1-12}$, $C_{1-16}$, $C_{1-18}$, $C_{1-20}$, $C_{1-24}$, $C_{2-3}$, $C_{2-6}$, $C_{2-12}$, $C_{2-16}$, $C_{2-18}$, $C_{2-20}$, or $C_{2-24}$ alkylene group. The alkylene group can be branched or unbranched. The alkylene group can also be substituted or unsubstituted. For example, the alkylene group can be substituted with one or more substitution groups, as described herein for alkyl.

By "amino" is meant —$NR^{N1}R^{N2}$, where each of $R^{N1}$ and $R^{N2}$ is, independently, H, optionally substituted alkyl, optionally substituted alkaryl, or optionally substituted aryl; or where a combination of $R^{N1}$ and $R^{N2}$, taken together with the nitrogen atom to which each are attached, form a heterocyclyl group, as defined herein.

By "aryl" is meant a group that contains any carbon-based aromatic group including, but not limited to, benzyl, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one, two, three, four, or five substituents independently selected from the group consisting of: (1) $C_{1-6}$ alkanoyl (e.g., —C(O)R, in which R is H or an optionally substituted alkyl, as defined herein); (2) $C_{1-6}$ alkyl; (3) $C_{1-6}$ alkoxy (e.g., —OR$^{Ak}$, in which R$^{Ak}$ is an optionally substituted alkyl, as defined herein); (4) $C_{1-6}$ alkoxy-$C_{1-6}$ alkyl (e.g., —R$^{a1}$OR$^{a2}$, in which R$^{a1}$ is an optionally substituted alkylene, as defined herein, and R$^{a2}$ is an optionally substituted alkyl, as defined herein); (5) $C_{1-6}$ alkylsulfinyl (e.g., —S(O)R$^{Ak}$, in which R$^{Ak}$ is an optionally substituted alkyl, as defined herein); (6) $C_{1-6}$ alkylsulfinyl-$C_{1-6}$ alkyl (e.g., —R$^{a1}$S(O)R$^{a2}$, in which R$^{a1}$ is an optionally substituted alkylene, as defined herein, and R$^{a2}$ is an optionally substituted alkyl, as defined herein); (7) $C_{1-6}$ alkylsulfonyl (e.g., —SO$_2$R$^{Ak}$, in which R is an optionally substituted alkyl, as defined herein); (8) $C_{1-6}$ alkylsulfonyl-$C_{1-6}$ alkyl (e.g., —R$^{a1}$SO$_2$R$^{a2}$, in which R$^{a1}$ is an optionally substituted alkylene, as defined herein, and R$^{a2}$ is an optionally substituted alkyl, as defined herein); (9) aryl; (10) amino; (11) $C_{1-6}$ aminoalkyl (e.g., —R$^{a1}$NR$^{N1}$R$^{N2}$, in which R$^{a1}$ is an optionally substituted alkylene, as defined herein, and R$^{N1}$ and R$^{N2}$ are any described herein); (12) heteroaryl; (13) $C_{1-6}$ alk-$C_{4-18}$ aryl (e.g., —R$^{a1}$R$^{Ar}$, in which R$^{a1}$ is an optionally substituted alkylene, as defined herein, and R$^{Ar}$ is an optionally substituted aryl, as defined herein); (14) aryloyl (e.g., —C(O)R$^{Ar}$, in which R$^{Ar}$ is an optionally substituted aryl, as defined herein); (15) azido (e.g., an —N$_3$ group); (16) cyano (e.g., a —CN group); (17) $C_{1-6}$ azidoalkyl (e.g., —R$^{a1}$N$_3$, in which R$^{a1}$ is an optionally substituted alkylene, as defined herein); (18) carboxyaldehyde (e.g., a —C(O)H group); (19) carboxyaldehyde-$C_{1-6}$ alkyl (e.g., —R$^{a1}$C(O)H, in which R$^{a1}$ is an optionally substituted alkylene, as defined herein); (20) $C_{3-8}$ cycloalkyl; (21) $C_{1-6}$ alk-$C_{3-8}$ cycloalkyl (e.g., —R$^{a1}$R$^{Cy}$, in which R$^{a1}$ is an optionally substituted alkylene, as defined herein, and R$^{Cy}$ is an optionally substituted cycloalkyl, as defined herein); (22) halo (e.g., F, Cl, Br, or I); (23) $C_{1-6}$ haloalkyl (e.g., an alkyl group, as defined herein, substituted with one or more halo); (24) heterocyclyl; (25) heterocyclyloxy (e.g., —OR$^{Het}$, in which R$^{Het}$ is an optionally substituted heterocyclyl, as defined herein); (26) heterocyclyloyl (e.g., —C(O)R$^{Het}$, in which R$^{Het}$ is an optionally substituted heterocyclyl, as defined herein); (27) hydroxyl (e.g., an —OH group); (28) $C_{1-6}$ hydroxyalkyl (e.g., an alkyl group, as defined herein, substituted by one to three hydroxyl groups, with the proviso that no more than one hydroxyl group may be attached to a single carbon atom of the alkyl group); (29) nitro (e.g., an —NO$_2$ group); (30) $C_{1-6}$ nitroalkyl (e.g., an alkyl group, as defined herein, substituted by one to three nitro groups); (31) N-protected amino; (32) N-protected amino-$C_{1-6}$ alkyl; (33) oxo (e.g., =O group); (34) $C_{1-6}$ thioalkoxy (e.g., —SR$^{Ak}$, in which R an optionally substituted alkyl, as defined herein); (35) thio-$C_{1-6}$ alkoxy-$C_{1-6}$ alkyl (e.g., —R$^{a1}$SR$^{a2}$, in which R$^{a1}$ is an optionally substituted alkylene, as defined herein, and R$^{a2}$ is an optionally substituted alkyl, as defined herein); (36) —(CH$_2$)$_r$CO$_2$R$^A$, where r is an integer of from zero to four, and R$^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (37) —(CH$_2$)$_r$CONR$^B$R$^C$, where r is an integer of from zero to four and where each R$^B$ and R$^C$ is independently selected from the group consisting of (a) hydrogen, (b) $C_{1-6}$ alkyl, (c) $C_{4-18}$ aryl, and (d) $C_{1-6}$ alk-$C_{4-18}$ aryl; (38) —(CH$_2$)$_r$SO$_2$R$^D$, where r is an integer of from zero to four and where R$^D$ is selected from the group consisting of (a) $C_{1-6}$ alkyl, (b) $C_{4-18}$ aryl, and (c) $C_{1-6}$ alk-$C_{4-18}$ aryl; (39) —(CH$_2$)$_r$SO$_2$NR$^E$R$^F$, where r is an integer of from zero to four and where each of R$^E$ and R$^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (40) —(CH$_2$)$_r$NR$^G$R$^H$, where r is an integer of from zero to four and where each of R$^G$ and R$^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group; (41) thiol (e.g., an —SH group); (42) perfluoroalkyl (e.g., an alkyl group, as defined herein, having each hydrogen atom substituted with a fluorine atom);

(43) perfluoroalkoxy (e.g., —OR$^F$, in which R$^F$ is an alkyl group, as defined herein, having each hydrogen atom substituted with a fluorine atom); (44) aryloxy (e.g., —OR$^{Ar}$, where R$^{Ar}$ is an optionally substituted aryl group, as defined herein); (45) cycloalkoxy (e.g., —OR$^{Cy}$, in which R$^{Cy}$ is an optionally substituted cycloalkyl, as defined herein); (46) cycloalkylalkoxy (e.g., —OR$^{a1}$R$^{Cy}$, in which R$^{a1}$ is an optionally substituted alkylene, as defined herein, and R$^{Cy}$ is an optionally substituted cycloalkyl, as defined herein); and (47) arylalkoxy (e.g., —OR$^{a1}$R$^{Ar}$, in which R$^{a1}$ is an optionally substituted alkylene, as defined herein, and R$^{Ar}$ is an optionally substituted aryl group, as defined herein). In particular embodiments, an unsubstituted aryl group is a $C_{4-18}$, $C_{4-14}$, $C_{4-12}$, $C_{4-10}$, $C_{6-18}$, $C_{6-14}$, $C_{6-12}$, or $C_{6-10}$ aryl group.

By "arylene" is meant a bivalent form of an aryl group, as described herein. Exemplary arylene groups include phenylene, naphthylene, biphenylene, triphenylene, diphenyl ether, acenaphthenylene, anthrylene, or phenanthrylene. In some embodiments, the arylene group is a $C_{4-18}$, $C_{4-14}$, $C_{4-12}$, $C_{4-10}$, $C_{6-18}$, $C_{6-14}$, $C_{6-12}$, or $C_{6-10}$ arylene group. The arylene group can be branched or unbranched. The arylene group can also be substituted or unsubstituted. For example, the arylene group can be substituted with one or more substitution groups, as described herein for aryl. An exemplary arylene group includes —(C$_6$H$_4$)$_n$— or —(C$_6$H$_3$)$_n$<, in which n is an integer between 1 and 10; as well as an optionally substituted —(C$_6$H$_4$)$_n$— or optionally substituted (C$_6$H$_3$)$_n$<, in which one or more H is substituted with one or more functional group (e.g., as described herein for an aryl group).

By "cycloalkyl" is meant a monovalent saturated or unsaturated non-aromatic cyclic hydrocarbon group of from three to eight carbons, unless otherwise specified, and is exemplified by cyclopropyl, cyclobutyl, cyclopentyl, cyclohexyl, cycloheptyl, bicyclo[2.2.1.]heptyl and the like. The cycloalkyl group can also be substituted or unsubstituted. For example, the cycloalkyl group can be substituted with one or more groups including those described herein for alkyl.

By "heteroalkyl" is meant an alkyl group, as defined herein, containing one, two, three, or four non-carbon heteroatoms (e.g., independently selected from the group consisting of nitrogen, oxygen, phosphorous, sulfur, or halo). Exemplary heteroalkyl groups include —$R^{a1}OR^{a3}$ and —$R^{a1}OR^{a2}OR^{a3}$, in which each of $R^{a1}$ and $R^{a2}$ is, independently, an optionally substituted alkylene and in which $R^{a1}$ is an optionally substituted alkyl.

By "heteroalkylene" is meant a divalent form of an alkylene group, as defined herein, containing one, two, three, or four non-carbon heteroatoms (e.g., independently selected from the group consisting of nitrogen, oxygen, phosphorous, sulfur, or halo).

By "heterocyclyl" is meant a 5-, 6-, or 7-membered ring, unless otherwise specified, containing one, two, three, or four non-carbon heteroatoms (e.g., independently selected from the group consisting of nitrogen, oxygen, phosphorous, sulfur, or halo). The 5-membered ring has zero to two double bonds and the 6- and 7-membered rings have zero to three double bonds. The term "heterocyclyl" also includes bicyclic, tricyclic and tetracyclic groups in which any of the above heterocyclic rings is fused to one, two, or three rings independently selected from the group consisting of an aryl ring, a cyclohexane ring, a cyclohexene ring, a cyclopentane ring, a cyclopentene ring, and another monocyclic heterocyclic ring, such as indolyl, quinolyl, isoquinolyl, tetrahydroquinolyl, benzofuryl, benzothienyl and the like. Heterocyclics include thiiranyl, thietanyl, tetrahydrothienyl, thianyl, thiepanyl, aziridinyl, azetidinyl, pyrrolidinyl, piperidinyl, azepanyl, pyrrolyl, pyrrolinyl, pyrazolyl, pyrazolinyl, pyrazolidinyl, imidazolyl, imidazolinyl, imidazolidinyl, pyridyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl, and the like.

By "organic moiety" is meant a molecule, a compound, or a functional group including at least one carbon.

Other features and advantages of the invention will be apparent from the following description and the claims.

DETAILED DESCRIPTION OF THE INVENTION

The present invention relates to methods of employing a metal-organic framework (MOF) to cleave one or more bonds in a test compound (e.g., carbon-oxygen bonds in, for instance, ethers). In particular embodiments, the reaction between the MOF and the test compound proceeds by way of a hydrogenolysis reaction in the presence of any useful hydrogen source (e.g., $H_2$, $NaBH_4$, etc.).

Figure 1:
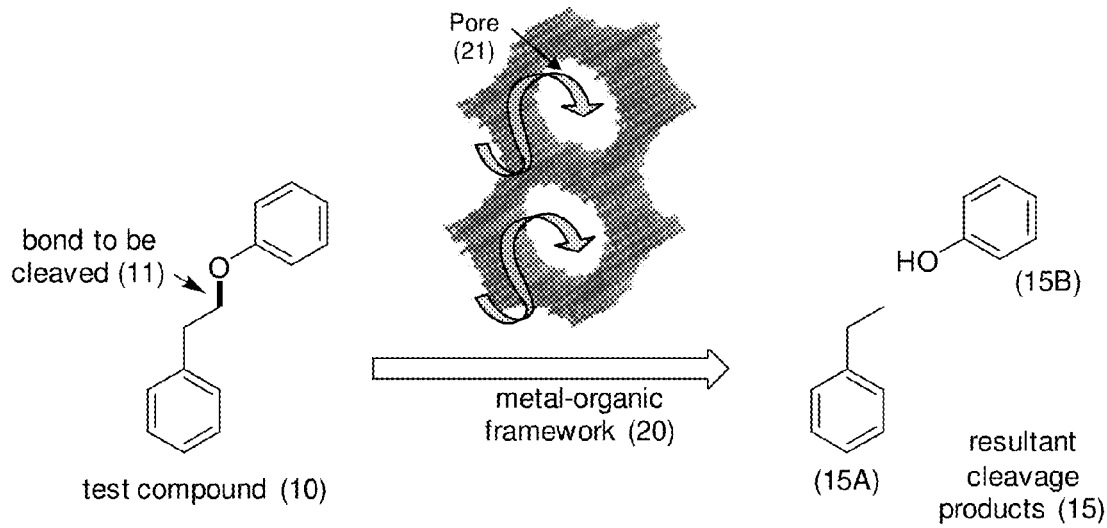
FIG. 1 shows a schematic of an exemplary method for employing a metal-organic framework (MOF) 20 to cleave a bond in a test compound 10.

FIG. 1 shows an exemplary method of cleaving a bond in a test compound. The method includes exposing a test compound 10 to a MOF 20 in the presence of a hydrogen source. The test compound can include any useful bond 11 (e.g., a carbon-oxygen bond) to be cleaved in the presence of the MOF-based catalyst. In some embodiments, the reaction can be facilitated by designing the MOF to have a pore 21 size that can accommodate the size (e.g., length) of the test compound 10.

Any useful reaction can be performed. In one instance, a hydrogenolysis reaction can be performed, in which the bond is cleaved by reaction with the hydrogen source. If the bond to be cleaved is a C—O bond, then bond scission occurs and resultant C—H and O—H bonds are formed.

As seen in FIG. 1, the reaction can also result in resultant cleavage products 15, in which cleavage of the bond 11 results in the formation of a C—H bond in resultant cleavage product 15A and an O—H bond in resultant cleavage product 15B. In some embodiments, each resultant cleavage product is, independently, an organic moiety.

The reaction can include the cleavage or scission of any useful bond (e.g., a carbon-carbon bond or a carbon-oxygen bond). The carbon-oxygen bond can by any useful bond, such as an ether bond (e.g., $R^1$—$OR^2$ or $R^2$—$OR^1$, in which each of $R^1$ and $R^2$ is, independently, an optionally substituted alkyl, optionally substituted alkaryl, or optionally substituted aryl; and in which the dash indicates the bond to be cleaved), or an aryl ether bond (e.g., $R^1$—$OR^2$ or $R^2$—$OR^1$, in which $R^1$ is an optionally substituted alkyl, optionally substituted alkaryl, or optionally substituted aryl; in which $R^2$ is optionally substituted alkaryl or optionally substituted aryl; and in which the dash indicates the bond to be cleaved).

In general, a MOF includes a plurality of nodes (e.g., metal nodes), an organic linker connecting at least two of the nodes, and an optional dopant comprising a second metal. Each node can include one or more metal atoms. The atom can have any useful valency, including those that are in an ionic form (e.g., a metal ion $M^{m+}$, in which m is any useful number, such as about 0.5, 1, 1.5, 2, 2.5, 3, 3.5, 4, 4.5, etc.), as well as be any useful metal. Furthermore, each node can have any useful number of coordination sites, in which none, one, or a plurality of such coordination sites may be unoccupied or open. Thus, each node can include one or more atoms, and each atom can, independently, include 0, 1, 2, or more open sites.

In addition, each node can include a cluster of metal atoms (e.g., a cluster of metal ions), in which one or more atoms within the cluster can be connected by an organic linker, a metal-metal bond, or a metal-ligand bond (e.g., wherein the ligand can be any useful moiety, such as an organic moiety, a solvent, a reactant, etc.). In some embodiments, one or more atoms within the cluster have an open metal site. In other embodiments, each cluster has at least one open metal site (e.g., in which each atom within that cluster can have either 0, 1, or more open metal sites, but at least one atom has 1 or more metal sites). In yet other embodiments, each atom in each cluster has at least one open metal site.

Any useful organic linker can be employed. In some instance, the linker includes a rigid backbone, as well as one or more functional moieties to bind to the node. Exemplary backbones includes optionally substituted arylene or heteroarylene groups (e.g., an optionally substituted —$(C_6H_4)_n$— or —$(C_6H_3)_n$<, in which n is an integer between about 1 and about 10; and optional substitutions include carboxyl, amino, hydroxyl, halide, alkynyl, etc.). Exemplary functional groups include hydroxyl, carboxyl (e.g., $CO_2H$), carboxyaldehyde, amino, etc. Non-limiting exemplary organic linkers include 2,5-dihydroxyterephthalic acid; 2,5-diaminoterephthalic acid; biphenyl-3,3',5,5'-tetracarboxylic acid; [1,1':4',1"]terphenyl-3,3",5,5"-tetracarboxylic acid; 4,4',4"-s-triazine-2,4,6-triyl-tribenzoic acid; 9,10-anthracenedicarboxylic acid; 1,2,4,5-tetrakis(4-carboxyphenyl)benzene; and trimesic acid.

Figure 2:
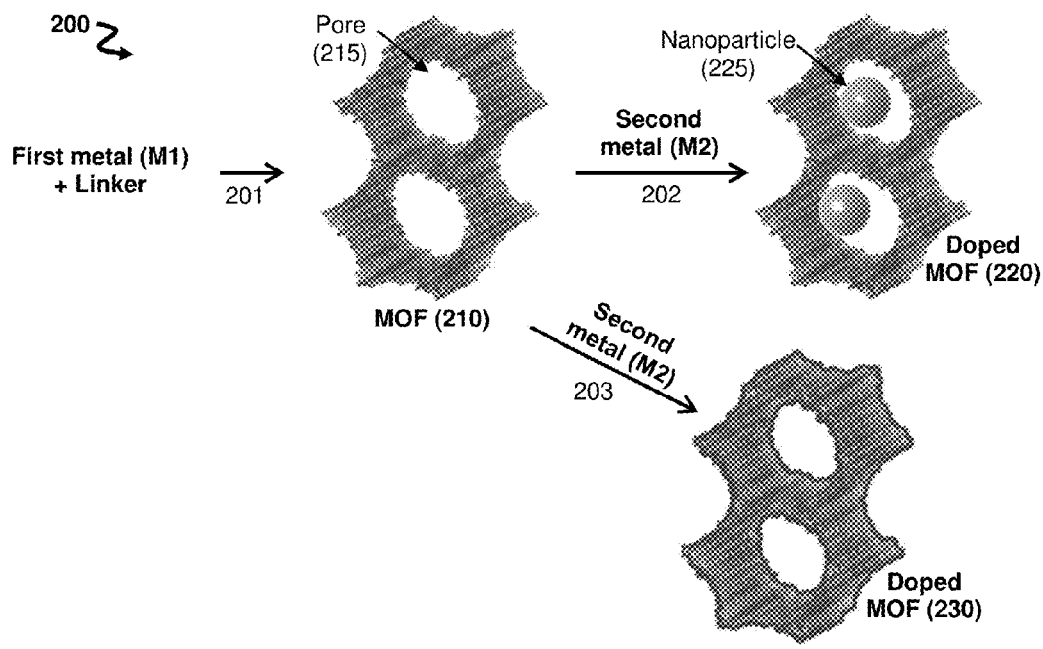
FIG. 2 shows a schematic of an exemplary MOF 210 and doped MOF 220,230.

FIG. 2 provides an exemplary schematic showing an MOF 210 formed from a first metal M1 (e.g., in which the first metal provides one or more atoms for each node) and an organic linker. In a first step of the method 200, the first metal M1 and linker is provided 201 to form the undoped MOF 210 having a pore 215. A second metal M2 can be introduced in any useful manner. In one instance 202, one or more M2 nanoparticles 225 are formed within the pores of the resultant doped MOF 220. In another instance 203, dispersed M2 metal atoms are deposited within the pores and/or surface of the resultant doped MOF 230.

The MOF can be synthesized and optionally doped in any useful manner. In one non-limiting instance, the MOF can be synthesized with a reagent including a first metal M1 (e.g., a metal salt, such as $M1(L)_l \cdot xX$, in which M1 is any metal herein, L is a ligand (e.g., nitrate, acetate, halide, etc.), X is a ligand (e.g., a solvent molecule, such as $H_2O$), and each of l or x is, independently, a number (e.g., about 0, 0.5, 1, 1.5, 2, 2.5, 3, 3.5, 4, 4.5, 5, 5.5, 6, 6.5, etc.). Any useful synthetic method can be employed, including solvothermal or hydrothermal conditions in any useful solvent (e.g., N,N-diethylformamide or N,N-dimethylformamide).

In addition, the resultant MOF can be doped in any useful manner, e.g., with a dopant M2 or a precursor including M2 (e.g., such as $M2(L)_l$, in which M2 is any metal herein, L is a ligand (e.g., nitrate, acetate, optionally substituted cyclopentadienyl, etc.), and l is a number (e.g., about 0, 0.5, 1, 1.5, 2, 2.5, 3, 3.5, 4, 4.5, 5, 5.5, 6, 6.5, etc.)

Metal M1 and M2 can be the same or different. Non-limiting exemplary metals for M1 and/or M2 include magnesium (e.g., $Mg^{2+}$), calcium (e.g., $Ca^{2+}$), strontium (e.g., $Sr^{2+}$), barium (e.g., $Ba^{2+}$), scandium (e.g., $Sc^{3+}$), titanium (e.g., $Ti^{3+}$), zirconium (e.g., $Zr^{4+}$), vanadium (e.g., $V^{2+}$, $V^{3+}$, or $V^{4+}$), chromium (e.g., $Cr^{2+}$ or $Cr^{3+}$), manganese (e.g., $Mn^{2+}$), rhenium (e.g., $Re^{2+}$), iron (e.g., $Fe^{3+}$), ruthenium (e.g., $Ru^{2+}$), cobalt (e.g., $Co^{2+}$), rhodium (e.g., $Rh^{2+}$), iridium (e.g., $Ir^{2+}$ or $Ir^{3+}$), nickel (e.g., $Ni^{2+}$), palladium (e.g., $Pd^{2+}$), platinum (e.g., $Pt^{2+}$), copper (e.g., $Cu^+$ or $Cu^{2+}$), silver (e.g., $Ag^+$), zinc (e.g., $Zn^{2+}$), cadmium (e.g., $Cd^{2+}$), aluminum (e.g., $Al^{3+}$), lead (e.g., $Pb^{2+}$), bismuth (e.g., $Bi^{3+}$), cerium (e.g., $Ce^{4+}$), etc., as well as combinations thereof and ionic forms thereof (e.g., monovalent, divalent, trivalent, tetravalent, pentavalent, hexavalent, ionic forms). Exemplary dopants include nickel and/or titanium, as well as ionic forms thereof.

Figure 11A:
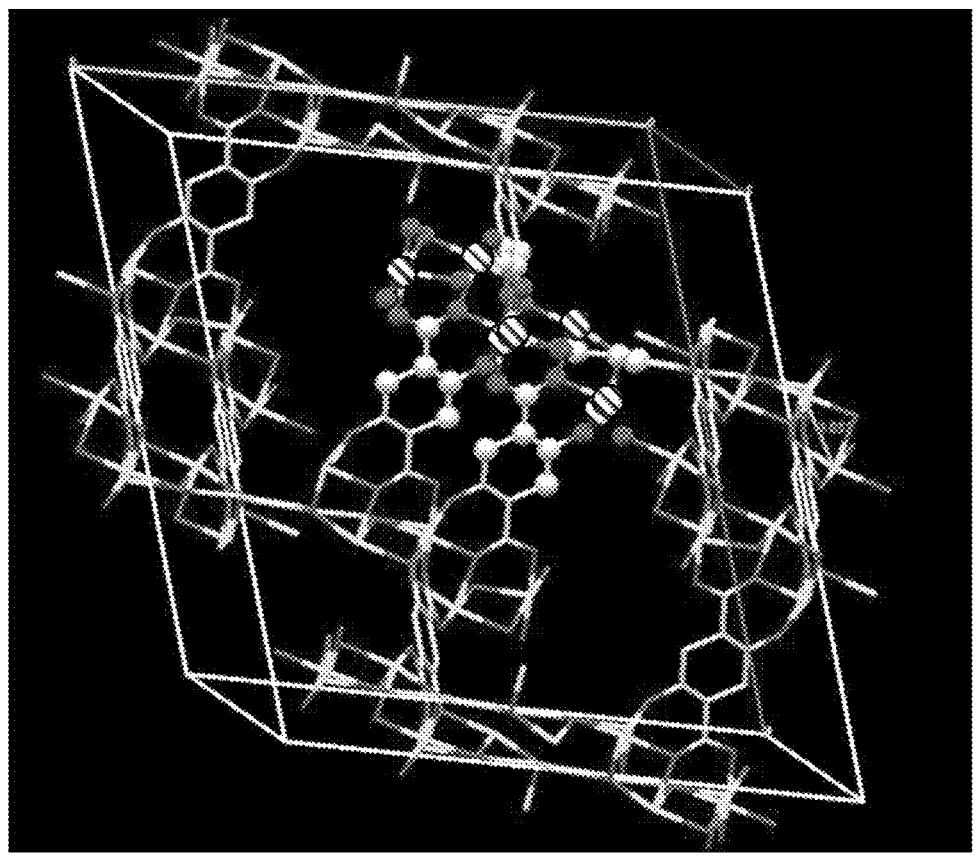
FIG. 11A-11C shows optimized geometries for IRMOF-74(I). Provided is (A) the structure of an IRMOF-74(I) cluster consisting of four nodes (four metal ions) coordinated to linkers, which approximates one side of the core unit of the hexagonal pore. Also provided are (B) the MOF pore structure 1100 formed by nodes 1110 (e.g., including a single metal atom or a metal cluster 1115) and organic linkers 1120; and (C) the organic linker 1120. For (A)-(C), hydrogen atoms are omitted for clarity; and the atom color code includes light gray for C, dark gray for O, and diagonal shading for Mg.
Figure 11B:
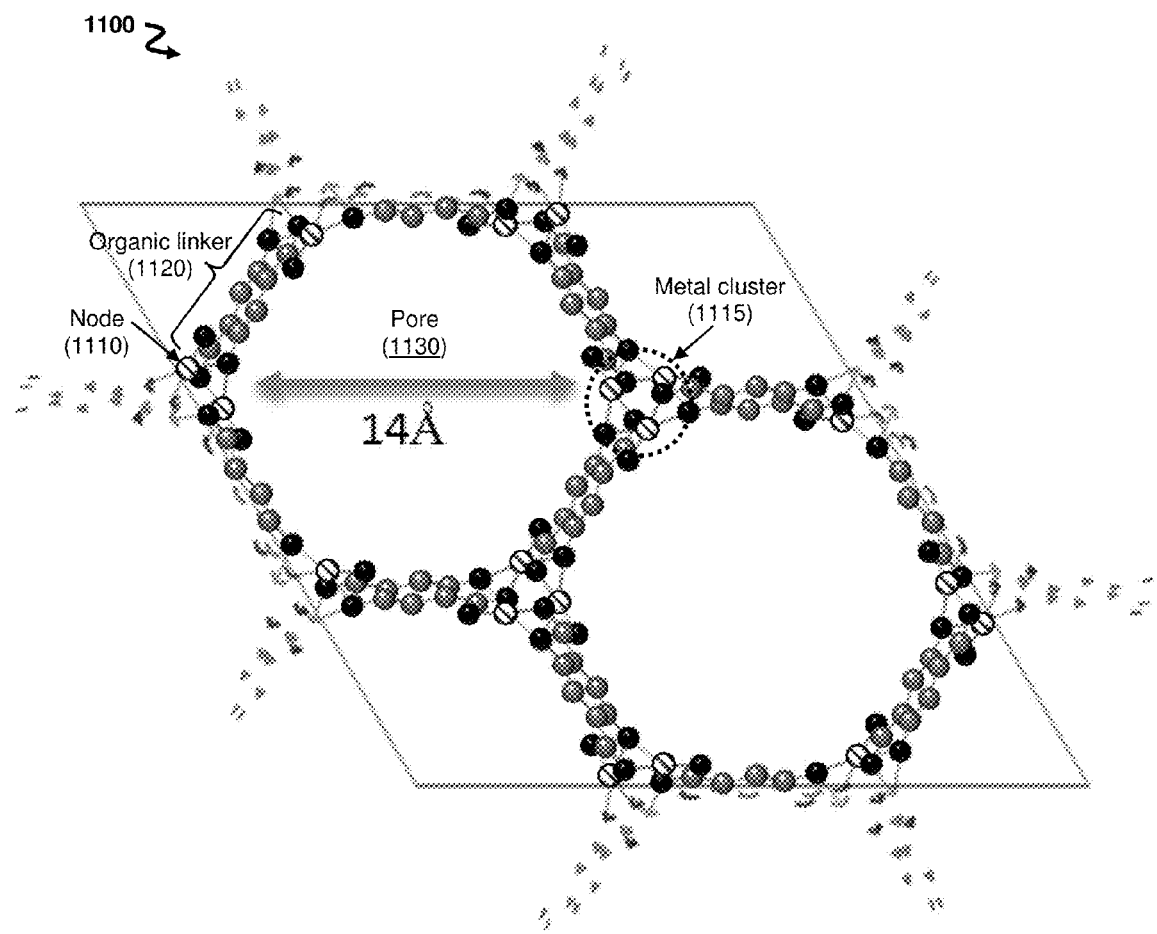
Figure 11C:
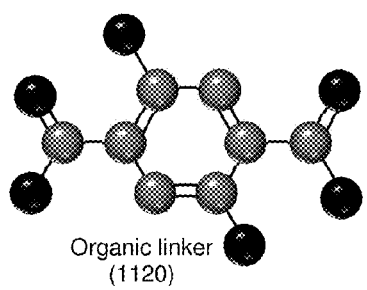

FIG. 11B provides an exemplary schematic of an MOF 1100 including a plurality of nodes 1110, in which an organic linker 1120 (see FIG. 11C) connects at least two of the nodes. This arrangement of nodes and linker provides a pore 1130. The rigidity of the linker can be controlled to provide a crystalline MOF. As can be further seen, a node can include a single metal atom or even a metal cluster 1115 having a plurality of metal atoms. Within the metal cluster 1115, metal atoms can be connected in any useful manner, such as by way of coordinating to the same organic linker, by way of metal-metal bonds, etc.

The reaction can be conducted in any useful solvent, such as an aromatic hydrocarbon (e.g., xylene, benzene, toluene, etc.) or an ionic liquid. Exemplary ionic liquids include a salt formed from any useful cation (e.g., dialkylimidazolium $[R^1R^2IM]^+$; dialkylpyridinium $[RPy]^+$; tetraalkylammonium $[NR_4]^+$; tetraalkylphosphonium $[PR_4]^+$; or cholinium $[Ch]^+$, as well as mixtures thereof, in which each of $R^1$, $R^2$, and R is, independently, an optionally substituted alkyl, optionally substituted heteroalkyl, optionally substituted alkoxy, optionally substituted hydroxyalkyl, as defined herein, such as methyl, ethyl, propyl, butyl, octyl, decyl, etc.) and any useful anion (e.g., acetate $[C_2H_3O_2]^-$; glycolate $[Glc]^-$; lysinate $[Lys]^-$; argininate $[Arg]^-$; alkylsulfate $[ROSO_3]^-$ in which R is H or an optionally substituted alkyl, as defined herein; halide $[X]^-$, such as fluoride, chloride, bromide, or iodide; dialkylphosphate $[(R^1O)(R^2O)PO_2]^-$ in which each of $R^1$ and $R^2$ is, independently, an optionally substituted alkyl, as defined herein; hexafluorophosphate $[PF_6]^-$; tetrafluoroborate $[BF_4]^-$; thiocyanate $[SCN]^-$; nitrate $[NO_3]^-$; methanesulfonate (mesylate) $[CH_3SO_3]^-$; trifluoromethane sulfonate or triflate $[CF_3SO_3]^-$ or $[TfO]^-$; bis-(trifluoromethanesulfonyl)imide $[Tf_2N]^-$; or dicyanamide $[N(CN)_2]^-$, as well as mixtures thereof). Additional ionic liquids are described in Tadesse H et al., "Advances on biomass pretreatment using ionic liquids: an overview," *Energy Environ. Sci.* 2011; 4:3913-29, which is incorporated herein by reference in its entirety.

The present invention also includes kits, such as those including a MOF (e.g., any described herein, including doped MOF) and instructions for employing the MOF with any useful test compound (e.g., biomass or a component thereof). The instructions can include any method described herein.

Biomass and Components Thereof

The methods herein can be employed to treat any useful mixture. In particular, the mixture can include one or more organic compounds, organic polymers, and/or biomass components. Exemplary biomass components include one or more moieties or compounds (e.g., organic moieties or organic compounds) derived, separated, or obtained from lignocellulosic biomass (e.g., plants, such as corn stalk, wheat straw, switchgrass, trees, etc.), algal biomass (e.g., chlorophyta, diatoms, plankton, protists, cyanobacteria, microalgae, macroalgae, diatoms, green algae, yellow algae, phytoplankton, haptophytes, etc.), Exemplary biomass components include lignin, cellulose, hemicellulose, proteins, carbohydrates, lipids, as well as fragments of any of these. Such components can be cleaved to form any useful resultant cleavage product, such as building blocks (e.g., monomers for polymers, platforms for pharmaceuticals, such as 2-hydroxymethylfuran, etc.), solvents, saccharides, alcohols (e.g., glycols, diols, etc.), fuel additives, biofuels, etc.

EXAMPLES

Example 1

MOF Catalysts for Selective Cleavage of Bonds in Biomass Components

Lignin is one of the most abundant source of renewable aromatics, with 200-300 Mtons per year projected production by a US biofuels industry that would process ~1B tons of biomass to meet DOE goals. However, there are currently no efficient processes for extracting these aromatics and converting them to value-added chemicals and drop-in fuels. The technical and economic challenges are staggering, due to the quantities of material involved and lignin's recalcitrance to depolymerization. Conventional lignin degradation processes use aggressive reagents, are energy intensive (e.g., requiring reaction temperatures of about 400-800° C.), and yield complex product mixtures. Milder reaction conditions and narrower product distributions could be achieved using lignin-degrading enzymes, but these can be too fragile to be practical for large-scale biorefining.

Metal-organic frameworks (MOFs) are crystalline materials with a nanoporous supramolecular structure consisting of metal ions connected by organic ligands (see, e.g., Furukawa H et al., "The chemistry and applications of metal-organic frameworks," *Science* 2013; 341(6149): 1230444 (12 pp.)). Their tailorable porosity, ease of synthesis, and ultra-high surface areas, combined with a broad choice of suitable building blocks make them promising materials for gas storage (see, e.g., Suh M P et al., "Hydrogen storage in metal-organic frameworks," *Chem. Rev.* 2012; 112:782-835; and Sumida K et al., "Carbon dioxide capture in metal-organic frameworks," *Chem. Rev.* 2012; 112:724-81); chemical separation (see, e.g., Li J R et al., "Selective gas adsorption and separation in metal-organic frameworks," *Chem. Soc. Rev.* 2009; 38:1477-504); chemical sensing (see, e.g., Kreno E et al., "Metal-organic framework materials as chemical sensors," *Chem. Rev.* 2012; 112:1105-25); and drug delivery (see, e.g., Horcajada P et al., "Metal-organic frameworks in biomedicine," *Chem. Rev.* 2012; 112:1232-68).

Recent work by several investigators demonstrates that MOFs can be effective catalysts for a variety of reactions (see, e.g., Lee J et al., "Metal-organic framework materials as catalysts," *Chem. Soc. Rev.* 2009; 38:1450-9). In most cases, however, the reactions catalyzed do not involve bond cleavage, as is required for decomposing lignin and fragments thereof that are produced by various methods currently under consideration for solubilizing the polymer.

In this Example, we describe MOF and metal-doped MOFs that catalyze the cleavage of aryl-ether bonds typical of those found in lignin. We demonstrate this reaction using lignin model compounds, which contain the key linkages that must be broken to convert lignin to small molecules. Non-limiting examples of these are shown in Scheme 1.

SCHEME 1

Examples of lignin model compounds having particular linkages

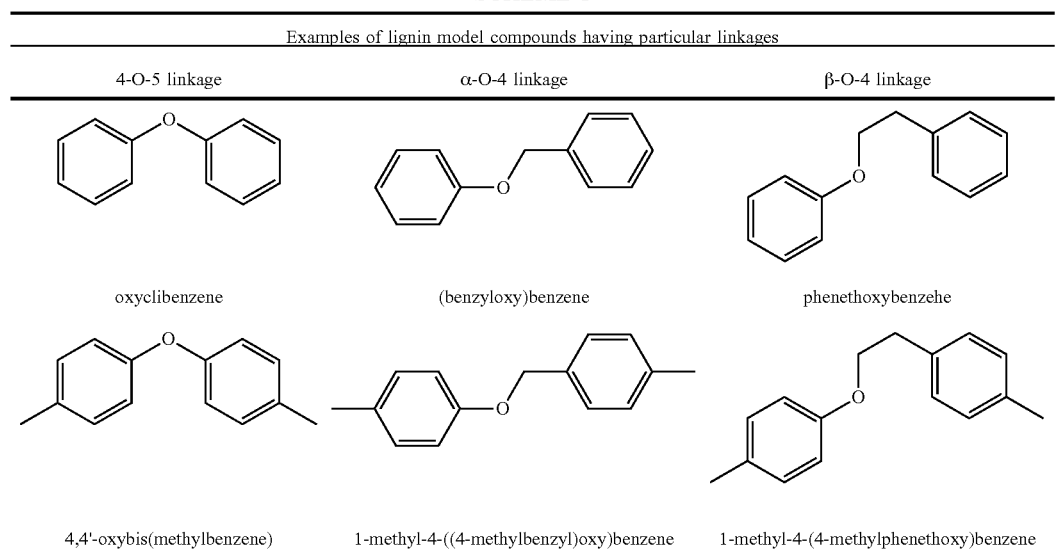

| 4-O-5 linkage | α-O-4 linkage | β-O-4 linkage |
|---|---|---|
| oxyclibenzene | (benzyloxy)benzene | phenethoxybenzehe |
| 4,4'-oxybis(methylbenzene) | 1-methyl-4-((4-methylbenzyl)oxy)benzene | 1-methyl-4-(4-methylphenethoxy)benzene |

To serve as a catalyst, several factors can be taken into consideration when selecting an appropriate MOF from the thousands of existing structures, or when designing a MOF for a specific reaction. First, the pores of the MOF must be large enough to accommodate the reactant. Consequently, MOFs with pore limiting diameters (PLD) above ~11 Å (the length of the model compounds) are probably required for compounds such as those in Scheme 1, although it is feasible for some to penetrate smaller pores if they enter endwise. Second, MOFs with one-dimensional, straight channels are expected to be beneficial, since this allows relatively unhindered transport of the reactant and product molecules into and out of the pores. Third, the MOF must be thermally and chemically stable under the reaction conditions.

Based on at least these criteria, we selected IRMOF-74-1(Mg) as a prototype MOF catalyst. The structure of this MOF includes $Mg^{2+}$ ions linked by dioxidobenzendicarboxylate anions (also known as 2,5-dihydroxyterephthalic acid). This MOF has unsaturated or open metal sites (OMS) that may serve as centers for chemical reaction. Another advantage is that other metal cations can be used instead of $Mg^{2+}$ (e.g., such as $Mn^{2+}$, $Fe^{2+}$, $Co^{2+}$, $Ni^{2+}$, $Cu^{2+}$, $Cd^{2+}$, $Zn^{2+}$, $Ca^{2+}$, $Sr^{2+}$, $Ba^{2+}$, etc.), which allows the reactivity of the catalyst to be modulated. Finally, the pores of this MOF are large enough to accommodate organometallic compounds, which once infiltrated into the pores, can be reduced to create metal nanoparticles. In prior work, we showed that this MOF is thermally stable under reducing (excess hydrogen) conditions and can also be doped with titanium using $TiCl_4$ (see, e.g., Stavila V et al., "Reversible hydrogen storage by $NaAlH_4$ confined within a titanium-functionalized MOF-74(Mg) nanoreactor," *ACS Nano* 2012; 6(11): 9807-17).

To illustrate these concepts, we performed catalytic reactions using three different MOF catalysts: IRMOF-74-1(Mg) (catalyst 1), $(TiCl_x)$@IRMOE-74-1(Mg) (catalyst 2), and (NiNP)@IRMOF-74-1(Mg) (catalyst 3), where catalyst 1 is the base MOF, activated to removed residual reactant following synthesis; catalyst 2 is catalyst 1 infiltrated with $TiCl_4$; and catalyst 3 is catalyst 1 infiltrated with dicyclopentadienylnickel ($NiCp_2$) and then reduced by $H_2$ to create nickel nanoparticles (NiNP) within the MOF pores. Characterization using powder x-ray diffraction (PXRD) shows that infiltration with these transition metal compounds does not damage the MOF. Both Ni- and Ti-doped MOFs remained porous following infiltration: 419 $m^2/g$ for catalyst 2 and 445 $m^2/g$ for catalyst 3, compared with 1530 $m^2/g$ for catalyst 1.

Cleavage of aryl-ether bonds was demonstrated using these three catalysts and the model compounds (benzyloxy)benzene (BOB) and phenethoxybenzene (PEB). Reactions were conducted within a stainless steel cell under $H_2$ pressure at a temperature of 120° C. for several hours. Products were detected using proton nuclear magnetic resonance (1H-NMR) and gas chromatography/mass spectrometry (GC-MS). Results for selected experiments are given in Table 1.

TABLE 1

Reaction conditions, products, and conversions for selected reactions

| Substrate | Catalyst | Conditions | Products | Conversion |
|---|---|---|---|---|
| BOB (α-O-4) | No catalyst | 120° C., 10 bar $H_2$ | — | 0 |
| BOB | MOF-74(Mg) | 120° C., 10 bar $H_2$ | $PhCH_3$ + PhOH | 4% |
| BOB | Ti@MOF-74(Mg) | 120° C., 10 bar $H_2$ | $PhCH_3$ + PhOH | 19% |
| BOB | | 120° C., 10 bar $H_2$ | $PhCH_3$ + PhOH | 56% |
| PEB (β-O-4) | No catalyst | 120° C., 10 bar $H_2$ | — | 0 |
| PEB | Ti@MOF-74(Mg) | 120° C., 10 bar $H_2$ | $PhCH_2CH_3$ + PhOH | 3% |
| PEB | Ti@MOF-74(Mg) | 120° C., 10 bar $H_2$ | $PhCH_2CH_3$ + PhOH | 4% |
| PEB | Ti@MOF-74(Mg) | 120° C., 10 bar $H_2$ | $PhCH_2CH_3$ + PhOH | 47% |

As seen in Table 1, no reaction is observed in the absence of catalyst. In the presence of catalyst 1, a small amount of conversion is observed for both reactants. Catalyst 2 increased conversion of BOB substantially relative to catalyst 1, but conversion of PEB was largely unaffected. Finally, catalyst 3 converted 56% of BOB and 47% of PEB. In all three cases, selectivity is very high.

Figure 7:
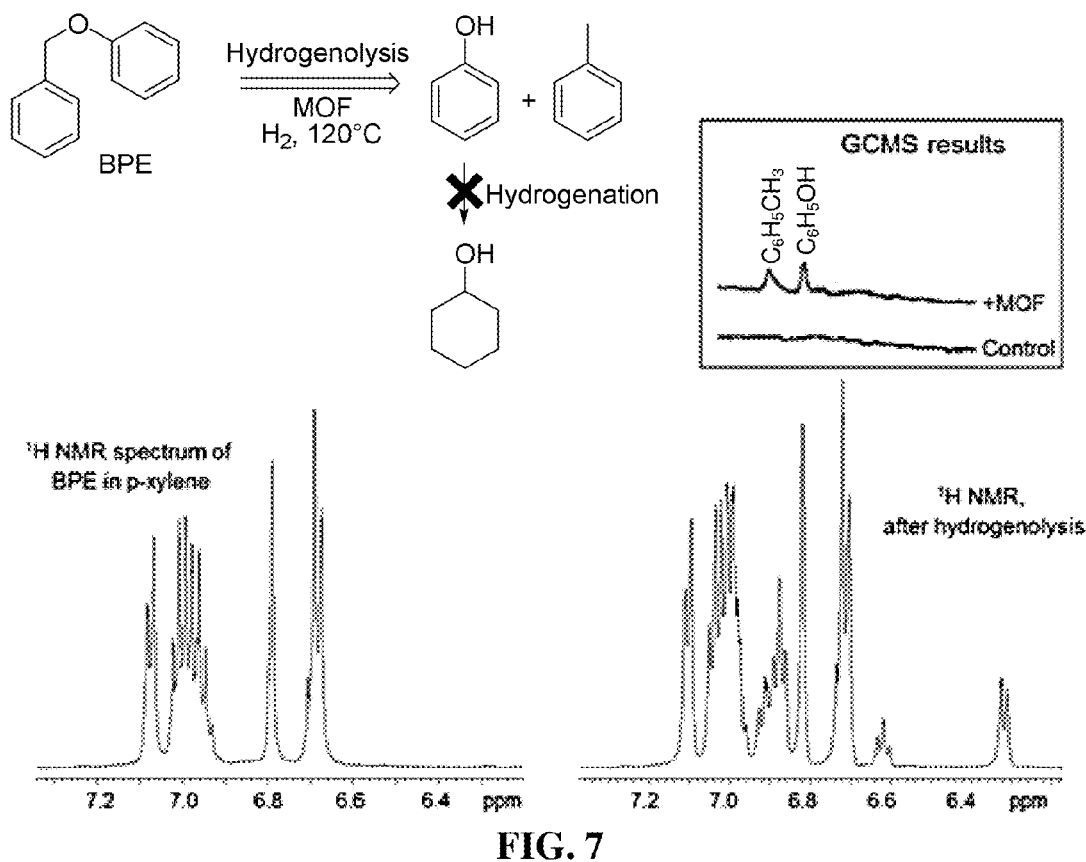
FIG. 7 shows a schematic of cleavage of a β-O-4 linkage in the BPE model compound by an MOF-based catalyst. Hydrogenation of the phenyl rings was not observed (black X), as occurs when using nickel nanoparticles in solution.

In particular, no evidence of ring hydrogenation was observed (FIG. 7). For example, we did not observe hydrogenation of the phenyl ring during hydrogenolysis of PEB using catalyst 3, in contrast with the results of He J et al., "Ni-catalyzed cleavage of aryl ethers in the aqueous phase," *J. Am. Chem. Soc.* 2012; 134:20768-75, who observed cyclohexane formation when using free nickel nanoparticles in solution as the catalyst.

The PXRD of the catalyst powder was unchanged following reaction in all cases, indicating that the MOF catalyst was stable on reaction conditions. This is consistent with previous work we reported in which catalyst 1 was exposed to high-pressure $H_2$ (see, e.g., (see, e.g., Stavila V et al., *ACS Nano* 2012; 6(11):9807-17). To our knowledge, this is the first demonstration of a bond cleavage reaction catalyzed by a MOF.

Example 2

Synthesis and Testing of MOF-Based Catalysts

MOF-based catalysts were synthesized with different length linkers, as well as different dopants. All air-sensitive manipulations were performed using standard glove-box and Schlenk line techniques under argon. All chemicals and solvents were obtained from commercial sources.

IRMOF-74(II)-Mg was isolated and activated following the published literature procedure using the reaction between $Mg(NO_3)_2 \cdot 6H_2O$ and 3,3'-dihydroxy-[1,1'-biphenyl]-4,4'-dicarboxylic acid in DMF (see, e.g., Deng H et al., "Large-pore apertures in a series of metal-organic frameworks," *Science* 2012; 336(6084):1018-23).

IRMOF-74(I)-Mg was synthesized from a solvothermal reaction of 2,5-dihydroxyterephthalic acid (98%, from Aldrich) with magnesium nitrate (99%, Aldrich) in a mixture of N,N-dimethylformamide (DMF) (99%, Acros), absolute ethanol (99.5%, Aldrich), and deionized water using a slightly modified literature protocol (see, e.g., Caskey S R et al., "Dramatic tuning of carbon dioxide uptake via metal substitution in a coordination polymer with cylindrical pores," *J. Am Chem. Soc.* 2008; 130:10870-1). $Mg(NO_3)_2 \cdot 6H_2O$ (0.729 g, 2.84 mmol) and 2,5-dihydroxyterephthalic acid (0.198 g, 1.0 mmol) were dissolved under sonication in a 20:1:1 (v/v/v) mixture of DMF (80 mL), ethanol (4 mL), and water (4 mL). The homogeneous solution was then transferred to a 150 mL Teflon-lined stainless-steel autoclave. The autoclave was capped tightly and heated to 125° C. in an oven. After 24 hours, the autoclave was removed from the oven; and a yellow microcrystalline material was recovered and washed with 10 mL DMF. The product was then soaked in 20 mL DMF and heated to 80° C. for 4 hours. The solvent was carefully decanted from the product and replaced with 20 mL methanol and stirred for 2 hours. Fresh methanol was used for solvent exchange for four more times. The yellow precipitate was isolated by filtration and washed thoroughly with methanol. The MOF was activated under a dynamic vacuum at 195° C. for 16 hours, yielding a yellow crystalline material.

Guest species infiltration was conducted as follows. $TiCl_4$ and $Cp_2Ni$ were loaded into the pores of IRMOF-74(I) and IRMOF-74(II) using vapor infiltration. First, the as-activated MOF was infiltrated with $TiCl_4$ or $Cp_2Ni$ vapors at 90° C. overnight. Next, the infiltrated IRMOF-74 material was loaded and sealed in a stainless-steel autoclave. The sealed autoclave was evacuated and filled with gaseous hydrogen at 1.0 MPa pressure. Then, the autoclave was heated to 95° C. and kept at that temperature for 2 hours. The catalyst samples obtained after impregnation with Ni and Ti species are referred hereafter as Ni@IRMOF-74(X) and Ti@IRMOF-74(X), where X=I or II. Nitrogen BET analysis indicated that the surface area of IRMOF-74(I) and IRMOF-74(II) was reduced from 1627 $m^2/g$ to 431 $m^2/g$ and 459 $m^2/g$ upon infiltration with Ti and Ni species, respectively. In the case of IRMOF-74(II), the surface area decreased from 1736 $m^2/g$ for the activated IRMOF-74(II) to 672 $m^2/g$ and 591 $m^2/g$ for Ti@IRMOE-74(II) and Ni@IRMOE-74 (II), respectively.

Catalytic tests were conducted as follows. The catalytic hydrogenolysis reactions were performed in a stainless steel reactor equipped with a hydrogen feed. In a typical procedure, 45 mg catalysts powder is loaded inside the reactor. Various substrates or test compounds were tested, including phenylethylphenyl ether (PPE), benzylphenyl ether (BPE), or diphenyl ether (DPE).

A solution of the corresponding substrate (PPE, BPE, or DPE) in 5.0 mL p-xylene was then added to the reactor. The reactor was pressurized with gaseous hydrogen, then sealed. The reactor was heated using a heating mantle equipped with thermocouples. After the reaction, the catalyst was filtered off; and the composition of the liquid fraction was analyzed by GCMS. Control reactions were performed, in which the substrate was present but no MOF catalysts were present. Such control reactions consistently showed 0% conversion (see, e.g., entry nos. 31-33 in Table 5).

MOF catalysts and reactions including such catalysts were characterized as follows. $^1H$ and $^{13}C$ NMR experiments were performed on a Varian 500 MHz spectrometer in $d_{10}$-xylene. GC-MS analysis was performed on an Agilent Varian CP-3800 Gas Chromatograph using a DB-WaxETR column (30 m×0.25 mm×0.5 µm) with output that was evenly split between a Saturn 2000R mass-spectrometer and an FID detector ($H_2$/air). Helium was used as a carrier gas, with a constant column flow of 1.2 mL/min. The column temperature control was adapted from the method detailed in Molinari V et al., "Titanium nitride-nickel nanocomposite as heterogeneous catalyst for the hydrogenolysis of aryl ethers," *J. Am. Chem. Soc.* 2014; 136(5):1758-61.

FID quantitation of the mass balance of products and reagents was achieved using individual and mixed standards with linear regression analysis of the integrated peak intensities. The MOF catalyst powders were characterized using scanning electron microscopy (SEM), X-ray diffraction (XRD), and energy dispersive X-ray spectroscopy (EDS). The powders were analyzed using a JEOL 7600 microscope (JEOL Ltd., Tokyo, Japan) operating at 15 kV. The XRD patterns were recorded on a PANalytical Empyrean X-ray diffractometer equipped with a PIXcel$^{3D}$ detector and operated at 45 kV and 40 mA using Cu Kα radiation (λ=1.5418 Å). Scattering intensities were measured using the Bragg-Brentano (θ-2θ) geometry with a step size of 0.026°. Surface area measurements (Brunauer, Emmett, and Teller (BET) method) were determined using a Micromeritics ASAP 2020 porosimeter. The composition in the gas phase in entry above the reaction was monitored by Residual Gas Analyzer RGA-100 from Stanford Research Systems. A minimal amount of gas sample in the reaction vessel was bled into the RGA at room temperature by a flow-restricted valve to ensure the gas pressure in RGA was below 5×10$^{-4}$ Pa, as required by the RGA instrument. Inductively coupled plasma optical emission spectrometry (ICP-OES) analysis was performed by ALS Environmental, Inc. For X-ray photoelectron spectroscopy (XPS) characterization, samples were pressed on pure indium foil substrate and then illuminated with an Al Kα source (Omicron model DAR400) using photons of 1490 eV. Photoelectrons were detected using a Physical Electronics model 10-360 electron energy analyzer. The slight charging resulting from the poor electrical conductivity of the samples was corrected by adjusting the binding energy of the most prominent C is peak to 284.8 eV. Peaks were fitted using CasaXPS software. Shirley-type background subtraction was used in all fits.

Figure 9A:
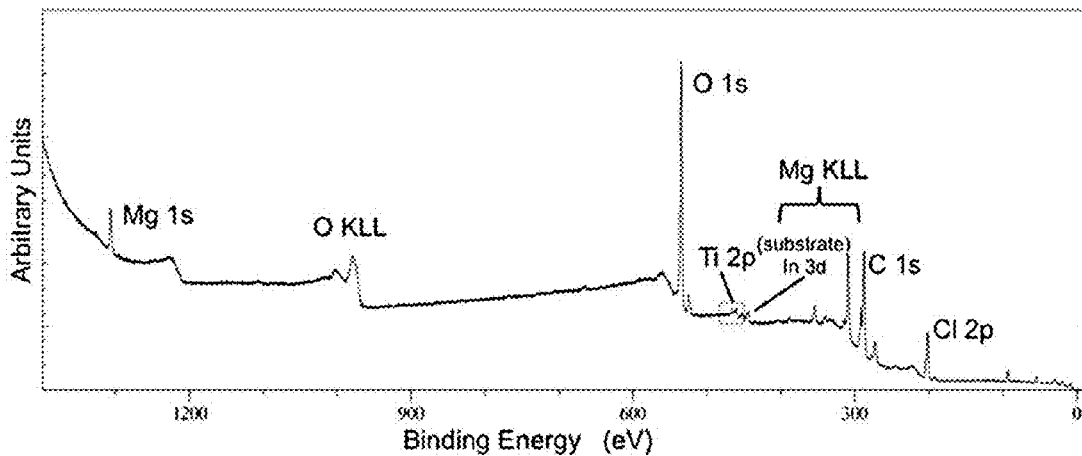
FIG. 9A-9C shows XPS spectra of various MOF-based catalysts. Provided are (A) an XPS spectrum of Ti@IRMOF-74(I); (B) an XPS spectrum of Ni@IRMOF-74(I); and (C) a graph showing expanded Ni 2p XPS features. The XPS spectra for Ni@IRMOF-74(I) samples were taken after 15, 30, and 300 seconds exposure to air. The data suggests that a significant amount of Ni in the MOF is in oxidation state (0).
Figure 9B:
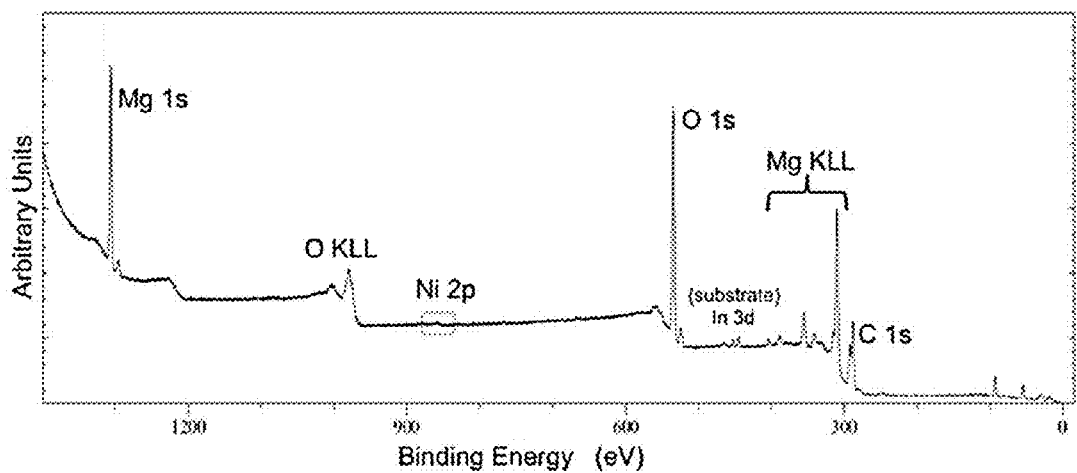
Figure 9C:
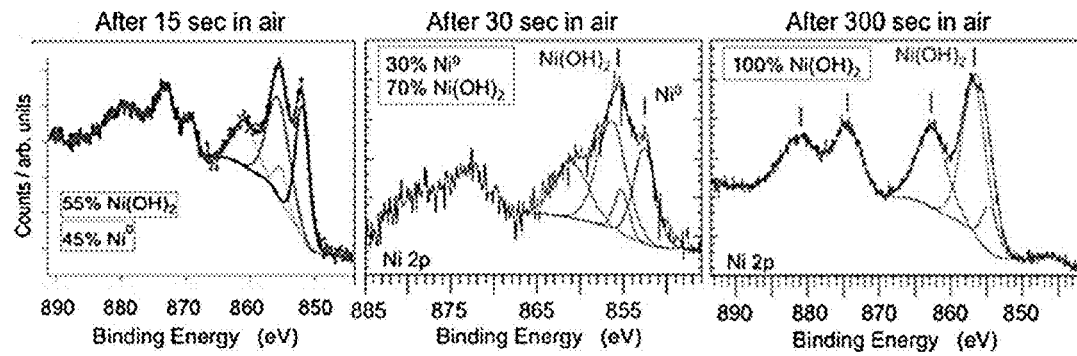

FIG. 9A-9C shows XPS spectra of various MOF-based catalysts. FIG. 9A shows the overall XPS spectrum of the Ti@IRMOF-74(I) sample with characteristic Mg, C, and O peaks from the MOF, as well as small Ti features from the dopant. FIG. 9B shows the entire XPS spectrum of Ni@IRMOF-74(I), again with the characteristic Mg, C, and O peaks from the MOF, as well as a small Ni contribution from the dopant. The Ti 2p XPS spectra from Ti@IRMOF-74(I) exhibit two prominent peaks centered at 457.5 eV (Ti $2p_{3/2}$) and 463.0 eV (Ti $2p_{1/2}$) characteristic of Ti(III)Cl$_3$ (e.g., Mousty-Desbuquoit C et al., "Electronic structure of titanium(III) and titanium(IV) halides studied by solid-phase x-ray photoelectron spectroscopy," *Inorg. Chem.* 1987; 26(8):1212-7).

FIG. 9C shows the characteristic Ni 2p features in the Ni@IRMOF-74(I) sample after exposure to air for 15 seconds (minimum amount of time required to transfer the sample to the XPS chamber), 30 seconds, and 300 seconds. FIG. 9C (left panel) shows two prominent Ni $2p_{3/2}$ peaks are located at 852.6 eV and 856.3 eV, corresponding to metallic Ni$^0$ (45%) and Ni(OH)$_2$ (55%), respectively (see, e.g., Biesinger M C et al., "Resolving surface chemical states in XPS analysis of first row transition metals, oxides and hydroxides: Cr, Mn, Fe, Co and Ni," *Appl. Surf Sci.* 2011; 257:2717-30; and Biesinger M C et al., "The role of the Auger parameter in XPS studies of nickel metal, halides and oxides," *Phys. Chem. Chem. Phys.* 2012; 14:2434-42). The quantification of the spectrum collected after 30 seconds exposure to air (middle panel in FIG. 9C) reveals that 70% of the Ni species near the surface (region probed by XPS) is in the Ni(OH)$_2$ phase, while 30% is metallic Ni. This is likely the result of metallic Ni nanoparticles oxidizing in air even after only 15 or 30 seconds of exposure, which is fully consistent with the literature on Ni nanoparticles (see, e.g., Phung X et al., "Surface characterization of metal nanoparticles," *Mater. Sci. Eng. A* 2003; 359(1-2):261-8). To verify the effect of air exposure, we prepared another identical Ni@IRMOF-74(I) sample that was exposed to air for 300 seconds (FIG. 9C, right panel), which clearly shows that all of the nickel was converted to Ni(OH)$_2$. No other Ni oxides were detected.

Example 3

Stability of MOF-Based Catalysts in Various Solvents

A mixture of activated IRMOF-74(I) powder (500 mg) in 20 g of the corresponding solvent (p-xylene, the ionic liquid 3-butyl-1-methyl-imidazolium acetate, or water) was placed in a glass flask equipped with a magnetic stirrer. The suspensions were stirred for 16 hours at 300 rpm at room temperature, then the solvent was removed and the MOF powders were washed with methanol and activated in vacuum. Weighting the recovered powders revealed that >99% of IRMOF-74(I) was recovered from the p-xylene and 3-butyl-1-methyl-imidazolium acetate mixtures, while in the case of IRMOF-74(I) in water only 79% or the powder was recovered, suggesting significant MOF dissolution. All recovered powders display XRD patterns essentially identical with the powder XRD of starting IRMOF-74(I) presented in FIG. 3B.

Example 4

Computational Modeling of MOF-Based Catalysis

MOF-based catalysts, test compounds, and cleavage products were also studied using computational modeling. The geometries of phenylethylphenyl ether (PPE), benzylphenyl ether (BPE), and diphenyl ether (DPE) representing the β-O-4, α-O-4, and 4-O-5 linkages in natural lignin, respectively, were optimized using the M06-2X hybrid exchange-correlation functional and the 6-31+G(d,p) basis set.

Figure 14:
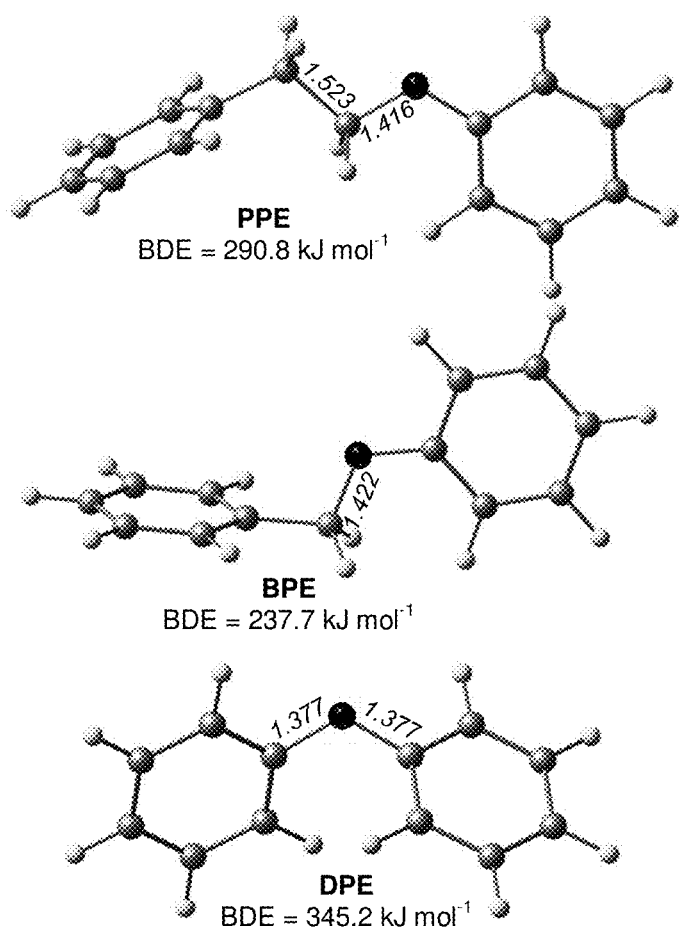
FIG. 14 shows optimized geometries and calculated gas-phase bond dissociation energies (BDE) at 393 K of the ether linkages in the aromatic ether model compounds: phenylethylphenyl ether (PPE), benzylphenyl ether (BPE), and diphenyl ether (DPE).

Optimized structures and C—O bond distances are given in FIG. 14. The geometries of all product species were also optimized. Vibrational frequencies were computed to verify that the computed structures corresponded to energy minima; no imaginary frequencies were found.

Bond dissociation energies (BDEs) for the ether bonds (C—O) were determined from the difference of the sum of the energies of the dissociated product fragments and the energy of the molecule:

$$BDE = \Delta H°_{BDE}(T) = (E_{Frag1} + E_{Frag2}) - E_{Mol}, \quad (Eq. 1)$$

where $E_{Mol}$ is the total energy of the molecule; and where $E_{Frag1}$ and $E_{Frag2}$ are the energies of the products resulting from cleavage of the C—O linkages, corrected to 393 K by including the zero-point energies (ZPE) and thermal contributions obtained from the computed frequencies.

Cluster models were also employed to assess the interaction between model compound and the MOFs. In particular, Mg-IRMOF-74(I) was simulated by a cluster including four $Mg^{2+}$ ions coordinated to five oxygen donor atoms from the linkers. This approximates one side of the core unit of hexagonal pore (FIG. 11A). The initial atom positions were taken from the experimental crystal structures (see, e.g., Deng H et al., *Science* 2012; 336(6084):1018-23; and Caskey S R et al., *J. Am Chem. Soc.* 2008; 130:10870-1) for IRMOF-74(I) (ref. code VOGTIV) and IRMOF-74(II) (ref. code RAVVUH). The cluster was then terminated by —H, —CH$_3$, and Li, following the method of Yu D et al., "A combined experimental and quantum chemical study of CO$_2$ adsorption in the metal-organic framework CPO-27 with different metals," *Chem. Sci.* 2013; 4:3544-56.

Cluster geometries, with and without the aromatic ether compounds, were then relaxed without any constraints and the binding energies computed from the relaxed geometries, using the hybrid QM/QM method at the MO6-2x/6-31G(d, p):PM6 levels of theory. For these calculations, the ONIOM ("Our own N-layered Integrated molecular Orbital and Molecular mechanics") approach implemented in Gaussian09 was used (Gaussian 09, Frisch M J et al., Gaussian, Inc., Wallingford Conn., 2009). During optimization of the various MOF-model compound complexes, the model compounds were treated at the MO6-2X/6-31+G(d,p) level of theory, whereas the MOF cluster was treated at the semi-empirical PM6 level of theory. The binding energies were then obtained at the MO6-2X/6-31+G(d,p) level of theory. The effects of solvent on the binding energies were computed using the integral equation formalism of the polarizable continuum model (IEF-PCM) into the self-consistent reaction field, where the solvent (xylene) was taken into account by means of a polarizable dielectric medium. Basis set superposition errors were removed in all binding energy calculations using the counterpoise method (see, e.g., Boys S F et al., "The calculation of small molecular interactions by the differences of separate total energies: some procedures with reduced errors," *Mol. Phys.* 1970; 19(4):553-66).

Charge transfer analysis was also conducted. According to density functional theory (DFT), chemical potential μ and chemical hardness η are defined as follows:

$$\mathcal{X} = -\mu = -\left(\frac{\partial E}{\partial N}\right)_{v(\vec{r})} \text{ and} \quad \text{(Eq. 2)}$$

$$\eta = \frac{1}{2}\left(\frac{\partial^2 E}{\partial N^2}\right)_{v(\vec{r})} = \frac{1}{2}\left(\frac{\partial \mu}{\partial N}\right)_{v(\vec{r})}, \quad \text{(Eq. 3)}$$

where E is the total energy of the system, N is the number of electrons in the system, $v(\vec{r})$ is the external potential, and μ is identified as the negative of the electronegativity χ (see, e.g., Parr R G & Yang W, "Density-functional theory of atoms and molecules," Oxford University Press, New York, N.Y., 1989 (352 pp.)).

By applying finite difference approximation to Eqs. (2) and (3), we get the operational definition for η and μ as follows:

$$\mu = -\frac{(IP + EA)}{2} \text{ and} \quad \text{(Eq. 4)}$$

$$\eta = \frac{(IP - EA)}{2}, \quad \text{(Eq. 5)}$$

where IP is the vertical ionization potential and EA is electron affinity.

Chemical potential and chemical hardness can be rewritten using Koopmans' theorem in terms of IP and EA as follows:

$$\eta = \frac{E_{LUMO} - E_{HOMO}}{2} \text{ and} \quad \text{(Eq. 6)}$$

$$\mu = \frac{E_{LUMO} + E_{HOMO}}{2}, \quad \text{(Eq. 7)}$$

where $E_{LUMO}$ is the lowest unoccupied molecular orbital's energy and $E_{HOMO}$ is the highest occupied molecular orbital's energy.

The global interactions between the MOF cluster model and aromatic ether model compounds were determined using the quantity ΔN, which represents the fractional number of electrons transferred from a system A to a system B, given as follows:

$$\Delta N = \frac{\mu_B - \mu_A}{2(\eta_B - \eta_A)} \quad \text{(Eq. 8)}$$

(see, e.g., Parr R G et al., "Absolute hardness: companion parameter to absolute electronegativity," *J. Am. Chem. Soc.* 1983; 105(26):7512-6).

We can also predict the flow of electrons using Sanderson's electronegativity equalization principle (see, e.g., Sanderson R T, "An interpretation of bond lengths and a classification of bonds," *Science* 1951; 114(2973):670-2), which states that there will be a flow of electrons from lower electronegativity (higher chemical potential) to that of higher electronegativity (lower chemical potential) until the electronegativity values are equalized to a value roughly equal to the geometric mean of the individual electronegativities, i.e., electrons will flow from molecule B to molecule A if $\chi_A > \chi_B$, where $\chi_A$ and $\chi_B$ are the electronegativities of the molecules A and B respectively.

Figure 13:
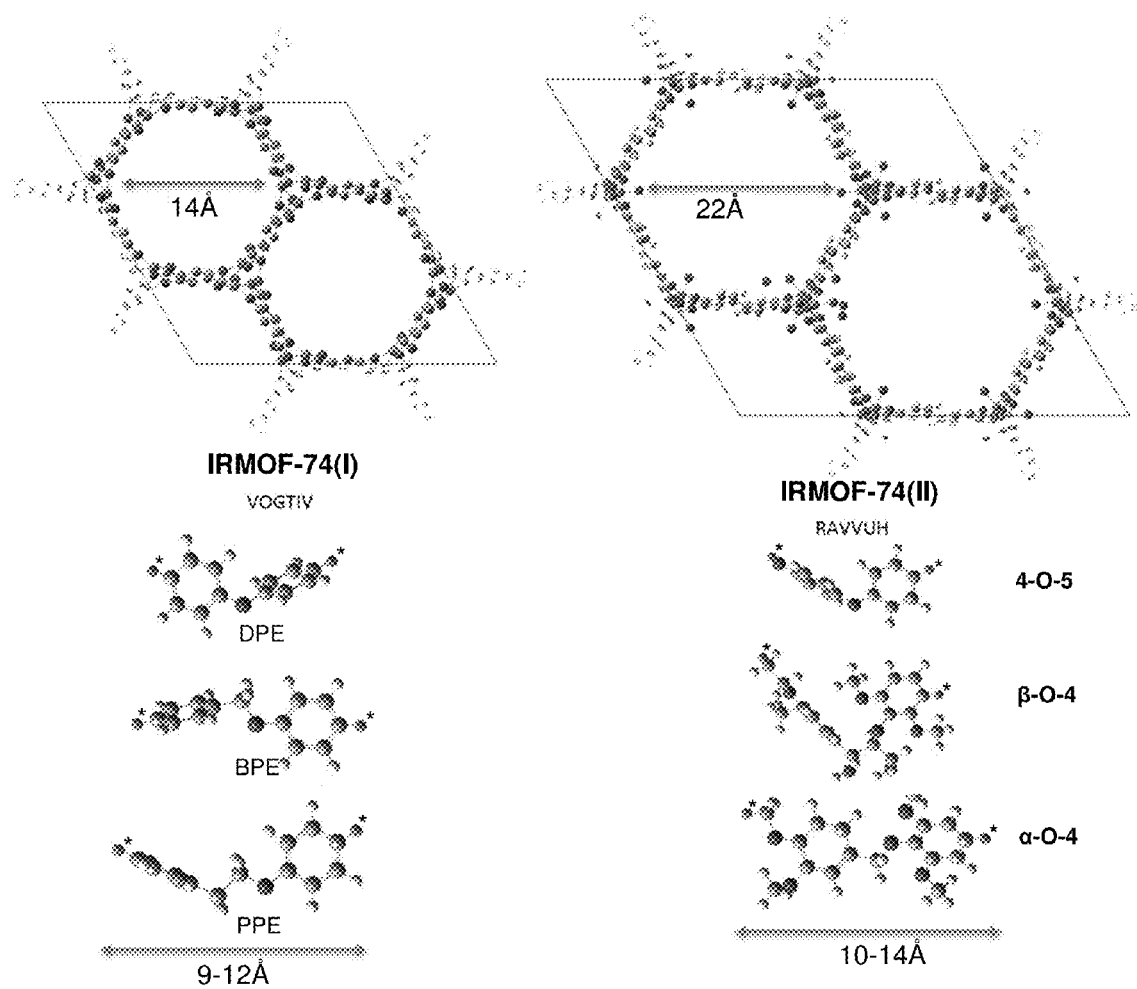
FIG. 13 shows (top) pore diameters of IRMOE-74(I) and IRMOE-74(II) and (bottom) largest intramolecular distances in the aromatic ether compounds, corresponding to a straight line between the atoms marked with an asterisk in the optimized geometries

Computational models were employed to determine substrate accessibility to MOF pores. We determined that the pores of the two MOFs were large enough to accommodate the all three aromatic ethers considered in this study, using experimentally determined crystal structures. FIG. 13 illustrates the pore size diameter of IRMOF-74(I) and IRMOF-74(II). The longest intramolecular distance in the optimized phenylethylphenyl ether, benzylphenyl ether, and diphenyl ether geometries corresponded to a straight line drawn between the atoms marked with an asterisk. These distances range between 9 Å and 14 Å; the substrates are therefore small enough to fit into the pores of both IRMOF-74(I) and IRMOF-74(I).

Reaction energies were also computationally calculated. The calculated gas-phase ether bond dissociation energies at 393 K are given in FIG. 14; and the calculated stabilization energies of the reactants ($H_2$+substrates) and products (hydrocarbon+phenol) in the presence of IRMOF-74(I) cluster model are shown in Table 2.

TABLE 2

Computed $\Delta H°_B$ at 393K of reactants and products

| | $\Delta H°_B$ [kJ/mol] of Reactants ($H_2$ + test compound) | | $\Delta H°_B$ [kJ/mol] of Products (hydrocarbon + PhOH) | |
|---|---|---|---|---|
| Substrate | in gas phase | with solvent (xylene) | in gas phase | with solvent (xylene) |
| PPE | 137.4 | 81.2 | 152.8 | 97.1 |
| BPE | 119.5 | 70.1 | 178.9 | 118.6 |
| DPE | 47.6 | 34.7 | 55.7 | 36.4 |

In particular, Table 2 shows calculated binding energies ($\Delta H°_B(T)$) at 393 K of the reactants ($H_2$+model compound or test compound) and products (hydrocarbon+phenol or PhOH) on the IRMOF-74 cluster model, relative to gas phase and in the presence of xylene solvent environment. The optimized geometry of ($H_2$+model compound) with the cluster was used to obtain the "gas phase" results. Results accounting for a xylene solvent environment were obtained by performing a single point calculation using the geometry used for the gas-phase calculation.

Figure 12A:
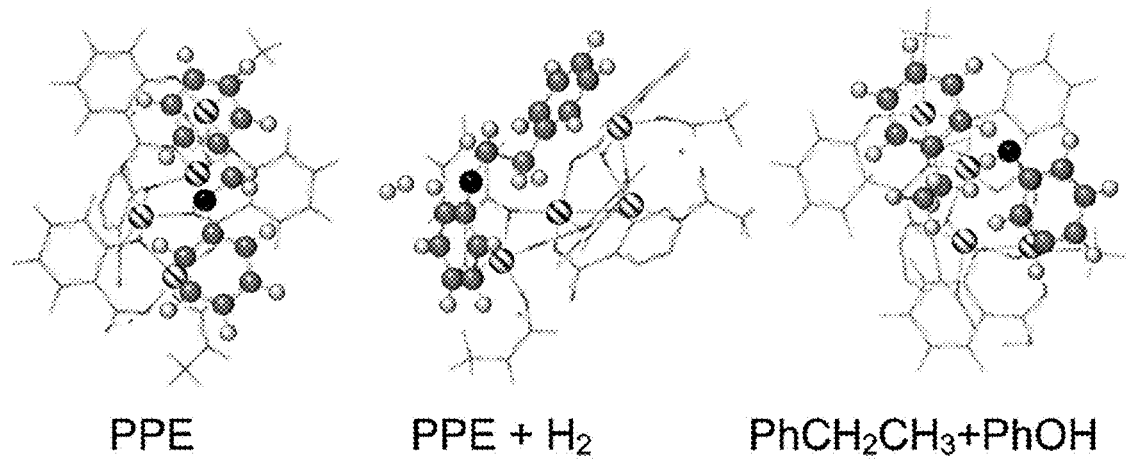
FIG. 12A-12B shows optimized gas-phase geometries for various model compounds, reactants, and products. Provided is (A) optimized geometries for adsorbed PPE, PPE+$H_2$, and the hydrogenolysis products, obtained using the QM/QM method. Substrate compounds and OMS on the MOF are shown as spheres versus the stick model of the cluster. Also provided is (B) optimized geometries of substrate-MOF cluster units (top and side views) using QM/QM method. Aromatic ether compounds and the metal nodes of the MOF cluster unit are highlighted for clarity. The atom color code includes diagonal shading for Mg, black for O, gray for C, and white for H.
Figure 12B:
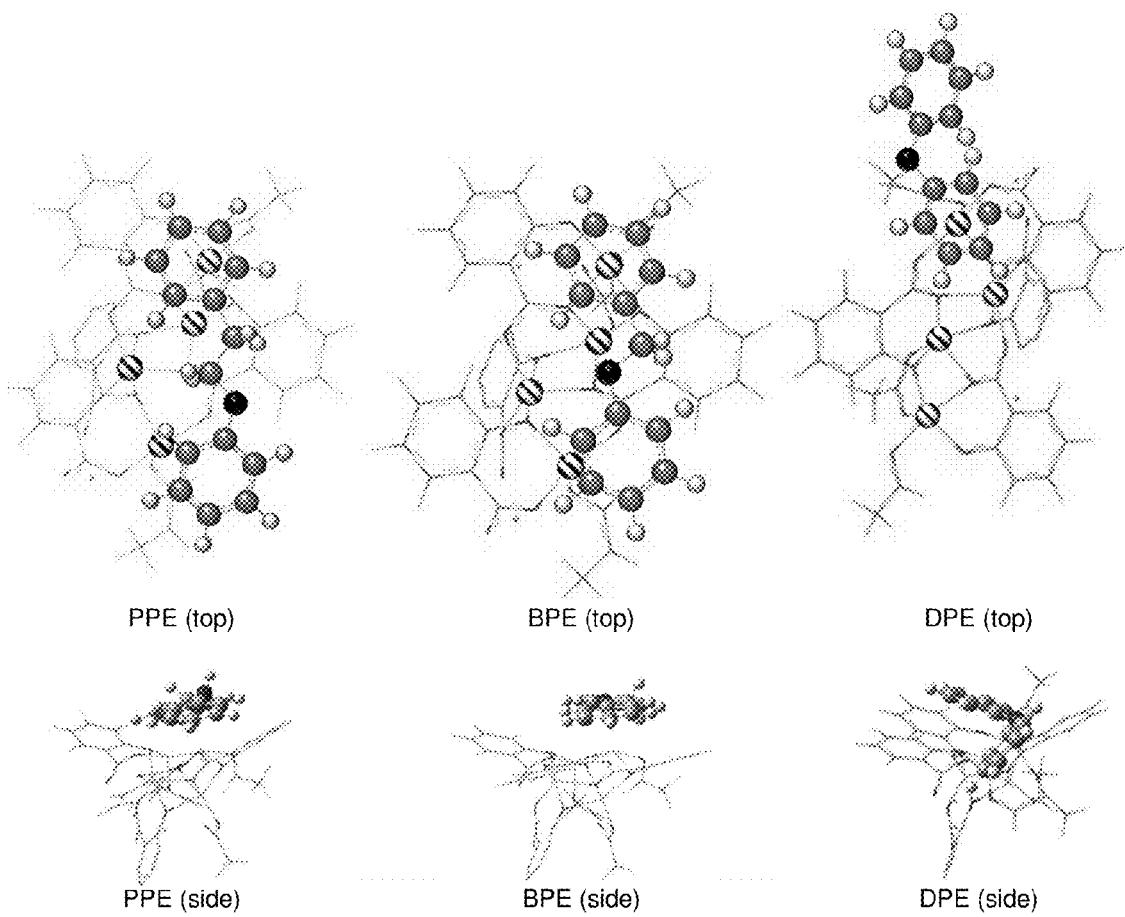

FIG. 12B shows configurations of aromatic ether compounds with the cluster model, determined by the QM/QM method described above. Among the three ether bond linkage types, diphenylether (4-O-5) has the shortest C—O bond distance (1.37 Å); the C—O bond distances in benzylphenylether (β-O-4) and phenylethylphenyl ether (α-O-4) are 1.41 Å and 1.42 Å, respectively. The computed BDE indicate that the ether linkages in the α-O-4 and β-O-4 model compounds are weaker than the 4-O-5 linkages, as reported previously (see, e.g., Phung X et al., *Mater. Sci. Eng. A* 2003; 359(1-2):261-8).

Figure 15:
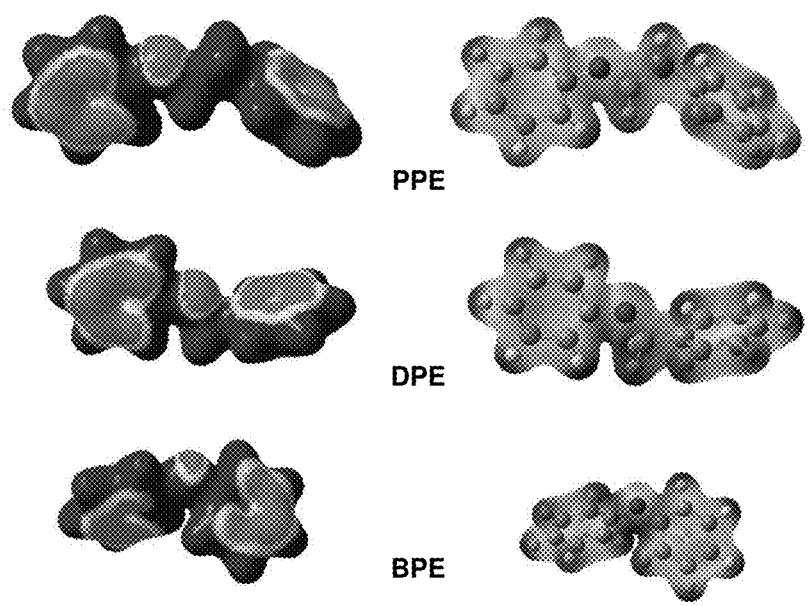
FIG. 15 shows molecular electrostatic potential maps (MESP) of aromatic ether compounds (in the absence of the MOF-74 cluster) at the ±0.02 au isosurface. The color scale indicates the charges on the atoms: gray for most negative, light gray for neutral, and dark gray for most positive charge

Molecular electrostatic potential (MESP) maps were also computed. FIG. 15 shows MESP maps for each aromatic ether compound in the gas phase, which indicates the distinct separation of positively and negatively charged regions in these molecules. Without wishing to be limited by mechanism, we expect that such distinctly charged regions will play a dominant role in interactions with the MOF.

Comparison with the optimized cluster-substrate geometries (e.g., as shown FIG. 12A-12B) indicated that the negative regions located on the rings are localized on the electron-accepting $Mg^{2+}$ open metal sites of the MOF cluster, whereas the negatively charged O atoms do not interact directly with the metal ions, probably for steric reason. However, this makes them accessible for electrophilic attack by $H_2$.

Charge transfer analysis ($\Delta N$) was also determined. The interactions between the selected aromatic ether compounds (A) and the MOF cluster (B) was also quantified by using the quantity N representing the fractional number of electrons transferred from A to B. Values of $\Delta N$ are presented in Table 3. In general, electrons flow from less electronegative regions to more electronegative ones. Combining this fact with the definition of $\Delta N$ (Eq. 8) showed that charge transfer values are negative for aromatic ether compounds, indicating that they are electron donors. In the interaction of the MOF cluster with aromatic model compounds, the MOF accepted the maximum charge from PPE, followed by BPE and DBE. This trend was consistent with the computed interaction energies of the model compounds with the MOF cluster, as well as with the observed trend in conversion.

TABLE 3

Charge transfer between aromatic ether compounds and MOF

| Substrate | Chemical hardness $\eta$ [eV] | Chemical potential $\mu$ [eV] | Charge transfer $\Delta N$ |
|---|---|---|---|
| PPE | 3.90 | −3.63 | −0.040 |
| BPE | 3.88 | −3.66 | −0.038 |
| DPE | 3.82 | −3.70 | −0.034 |
| MOF Cluster Model | 1.84 | −4.09 | |

Example 5

MOF-Based Catalysts for Selective Hydrogenolysis of Carbon-Oxygen Ether Bonds

In this Example, we demonstrate that metal-organic frameworks (MOFs) can catalyze hydrogenolysis of aryl ether bonds under mild conditions. Mg-IRMOF-74(I) and Mg-IRMOF-74(II) are stable under reducing conditions and can cleave phenyl ethers containing β-O-4, α-O-4, and 4-O-5 linkages to the corresponding hydrocarbons and phenols. In particular conditions, reactions occurred at 10 bar $H_2$ and 120° C. without added base. DFT-optimized structures and charge transfer analysis suggest that the MOF orients the substrate near $Mg^{2+}$ ions on the pore walls. Ti and Ni doping further increased conversions to as high as 82% with 96% selectivity for hydrogenolysis versus ring hydrogenation. Repeated cycling induced no loss of activity, making this a promising route for mild aryl-ether bond scission. Additional details follow.

The catalytic properties of nanoporous materials known as MOFs are attracting considerable attention as a result of their exceptional chemical and structural versatility (see, e.g., Liu J et al., "Applications of metal-organic frameworks in heterogeneous supramolecular catalysis," *Chem. Soc. Rev.* 2014; 43:6011-61; and Zhao Metal., "Porous metal-organic frameworks for heterogeneous biomimetic catalysis," *Acc. Chem. Res.* 2014; 47:1199-207). In some embodiments, MOFs are crystalline materials including metal ions coordinated to bridging organic linkers, forming a microporous or mesoporous structure. These materials offer an exceptionally high degree of synthetic versatility, enabling rational design of pore dimensions and chemistry to achieve product selectivity with high turnover rates. MOFs have remarkably high thermal and chemical stability (some are stable to temperatures as high as 500° C., see, e.g., Furukawa H et al., "The chemistry and applications of metal-organic frameworks," *Science* 2013; 341:1230444 (12 pp.); and Colombo V et al., "High thermal and chemical stability in pyrazolate-bridged metal-organic frameworks with exposed metal sites," *Chem. Sci.* 2011; 2:1311-9). Water stability, an issue with some frameworks, is no longer a limiting factor; a large number of water-stable MOFs are now known, some of which are unaffected by boiling in acidic or basic solution, and strategies for improving water stability in those that are not are now available (see, e.g., Burtch N C et al., "Water stability and adsorption in metal-organic frameworks," *Chem. Rev.* 2014; 114:10575-612).

MOFs can also serve as hosts for metal nanoparticles (NPs) known to catalyze hydrogenation reactions (see, e.g., Aijaz A et al., "Catalysis with metal nanoparticles immobilized within the pores of metal-organic frameworks," *J. Phys. Chem. Lett.* 2014; 5:1400-11; Guo Z et al., "Pt nanoclusters confined within metal-organic framework cavities for chemoselective cinnamaldehyde hydrogenation," *ACS Catal.* 2014; 4:1340-8; and Barta K et al., "Catalytic conversion of nonfood woody biomass solids to organic liquids," *Acc. Chem. Res.* 2014; 47(5):1503-12). Compared with catalysts supported on amorphous substrates, MOFs possess uniform cavities and a high density of reactive centers, which should contribute to increased turnover rates and selectivities (see, e.g., Gascon J et al., "Metal organic framework catalysis: quo vadis?,"*ACS Catal.* 2014; 4:361-78; and Stavila V et al., "Reversible hydrogen storage by $NaAlH_4$ confined within a titanium-functionalized MOF-74 (Mg) nanoreactor,"*ACS Nano* 2012; 6(11):9807-17).

As a result of these attractive properties, many types of MOF-catalyzed reactions are known, including oxidation, silylation, sulfurization, epoxidation, cycloaddition, and condensation, to name just a few (see, e.g., Liu J et al., *Chem. Soc. Rev.* 2014; 43:6011-61; Zhao M et al., *Acc. Chem. Res.* 2014; 47:1199-207; Furukawa H et al., *Science* 2013; 341:1230444 (12 pp.); Gascon J et al., *ACS Catal.* 2014; 4:361-78; and Corma A et al., "Engineering metal organic frameworks for heterogeneous catalysis," *Chem. Rev.* 2010; 110:4606-55). Notably absent from this list are simple bond-cleavage reactions, in particular hydrogenolysis, which is used extensively industrially to remove sulfur from hydrocarbons and has gained attention for production of value-added chemicals from lignocellulosic biomass (see, e.g., Higman C et al., "Advances in coal gasification, hydrogenation, and gas treating for the production of chemicals and fuels," *Chem. Rev.* 2014; 114:1673-708; and Ruppert A M et al., "Hydrogenolysis goes bio: from carbohydrates and sugar alcohols to platform chemicals," *Angew. Chem. Int. Ed.* 2012; 51:2564-601).

To our knowledge, there is only one report of MOF-catalyzed hydrogenation of an organic molecule (as opposed to organometallic precursors of metal nanoparticles); in this case, the catalytic reaction occurs in the presence of a sacrificial base (see, e.g., Park Y K et al., "Catalytic nickel nanoparticles embedded in a mesoporous metal-organic framework," *Chem. Commun.* 2010; 46:3086-88). In this Example, we describe experiments and modeling supporting the notion that MOFs can be effective catalysts for the hydrogenolysis of C—O aromatic ether bonds, which are common linkages in biomass.

MOF-74 was selected as a starting point for catalyst development because this topology has several advantages. First, the recently reported isoreticular IRMOF-74(n) series provides hexagonal 1-D channels with diameters between 1.2 and 9.8 nm that can accommodate a range of substrate sizes (see, e.g., Deng H et al., "Large-pore apertures in a series of metal-organic frameworks," *Science* 2012; 336 (6084):1018-23). Second, the density of open metal sites (OMS) in these MOFs, which can behave as Lewis acids to activate C—O bonds, is the highest known for this class of materials. Third, IRMOF-74(n) can be synthesized with a wide range of metals, (e.g., Mg, Mn, Fe, Co, Ni, Cu, and/or Zn), as well as mixed-metal compounds of up to 10 different metals, 16 allowing the reactivity of the OMS to be readily tuned (see, e.g., Wang L J et al., "Synthesis and characterization of metal-organic framework-74 containing 2, 4, 6, 8, and 10 different metals," *Inorg. Chem.* 2014; 53:5881-3). Finally, we recently demonstrated that Mg-MOF-74 had exceptional thermal and chemical stability, withstanding melt-infiltration with the highly reactive metal hydride $NaAlH_4$ (see, e.g., Stavila V et al., *ACS Nano* 2012; 6(11): 9807-17). Moreover, when doped with a titanium halide, this MOF reversibly catalyzed the rehydrogenation of the NaH and Al products into $NaAlH_4$, possibly by activating hydrogen or generating mobile reactive species. The detailed reaction data, catalyst characterization, and mechanism discussion presented here follow a limited and preliminary report by our team (see, e.g., Allendorf M D et al., "Bioinspired MOF-based catalysts for lignin valorization," *Sandia Report No.* SAND2014-18259, 2014 (27 pp.)).

Figure 6:
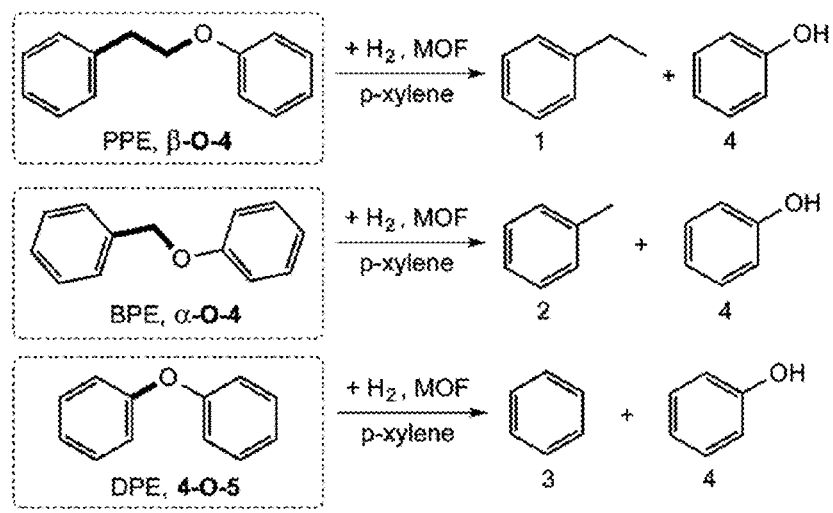
FIG. 6 shows exemplary hydrogenolysis reactions catalyzed by IRMOF-74(I, II).

We selected phenylethylphenyl ether (PPE), benzylphenyl ether (BPE), and diphenyl ether (DPE) as representative substrates which incorporate the β-O-4, α-O-4, and 4-O-5 (or 4,4') linkages found in lignin (FIG. 6).

In addition to the pure MOFs, we also prepared IRMOF-74(I) and IRMOF-74(II) samples infiltrated with $TiCl_x$ and Ni NPs, which were previously shown to catalyze aryl ether hydrogenolysis (see, e.g., Molinari V et al., "Titanium nitride-nickel nanocomposite as heterogeneous catalyst for the hydrogenolysis of aryl ethers," *J. Am. Chem. Soc.* 2014; 136(5):1758-61; Wang X et al., "Solvent effects on the hydrogenolysis of diphenyl ether with Raney nickel and their implications for the conversion of lignin," *Chem Sus Chem* 2012; 5:1455-66; and Sergeev A G et al., "A heterogeneous nickel catalyst for the hydrogenolysis of aryl ethers without arene hydrogenation," *J. Am. Chem. Soc.* 2012; 134:20226-9). The infiltration of Ti species was performed using our previously described procedure (see, e.g., Stavila V et al., *ACS Nano* 2012; 6(11):9807-17), in which $TiCl_4$ is vapor-infiltrated into the pores of the activated MOF, followed by treatment with gaseous hydrogen at 90° C. The insertion of Ni was achieved using methods pioneered by Fischer's group to create metal NPs in MOFs (see, e.g., Meilikhov M et al., "Metals @MOFs—loading MOFs with metal nanoparticles for hybrid functions," *Eur. J. Inorg. Chem.* 2010; 24:3701-14).

The as-synthesized MOF-based catalysts were evaluated for their catalytic activity in hydrogenolysis reactions with the PPE, BPE, and DPE substrates, results of which are given in Table 4. The reactions were performed in stainless steel cells loaded with the substrate compound in p-xylene and the MOF catalyst. Mixtures were pressurized with $H_2$ and heated to 90–120° C., well within the stability range for the IRMOF-74(I,II) materials (see, e.g., Deng H et al., *Science* 2012; 336(6084):1018-23). In all cases, the reactor pressure was 10 bar $H_2$; such pressures are commonly used in industrial hydrogenation reactions, including many heterogeneous catalysis processes (see, e.g., Wang D S et al., "Asymmetric hydrogenation of heteroarenes and arenes," *Chem. Rev.* 2012; 112:2557-90).

TABLE 4

Catalytic effect of MOFs on hydrogenolysis of aryl-ether compounds

| No. | Catalyst | Substrate | T [° C.] | t [h] | Conv. [%] | Selectivity 1 | 2 | 3 | 4 |
|---|---|---|---|---|---|---|---|---|---|
| 1 | IRMOF-74(I) | PPE | 120 | 16 | 12 | 87 | | | 91 |
| 2 | Ti@IRMOF-74(I) | PPE | 120 | 16 | 51 | 89 | | | 90 |
| 3 | Ni@IRMOF-74(I) | PPE | 120 | 16 | 68 | 91 | | | 94 |
| 4 | IRMOF-74(II) | PPE | 120 | 16 | 39 | 83 | | | 87 |
| 5 | Ti@IRMOF-74(II) | PPE | 120 | 16 | 60 | 79 | | | 83 |
| 6 | Ni@IRMOF-74(II) | PPE | 120 | 16 | 82 | 96 | | | 98 |
| 7 | IRMOF-74(I) | BPE | 120 | 16 | 10 | | 78 | | 84 |
| 8 | Ti@IRMOF-74(I) | BPE | 120 | 16 | 33 | | 75 | | 79 |
| 9 | Ni@IRMOF-74(I) | BPE | 120 | 16 | 57 | | 82 | | 85 |
| 10 | IRMOF-74(II) | BPE | 120 | 16 | 17 | | 73 | | 78 |
| 11 | Ti@IRMOF-74(II) | BPE | 120 | 16 | 42 | | 84 | | 89 |
| 12 | Ni@IRMOF-74(II) | BPE | 120 | 16 | 76 | | 91 | | 95 |
| 13 | IRMOF-74(I) | DPE | 120 | 16 | 4 | | | 79 | 82 |
| 14 | Ti@IRMOF-74(I) | DPE | 120 | 16 | 19 | | | 81 | 85 |
| 15 | Ni@IRMOF-74(I) | DPE | 120 | 16 | 29 | | | 80 | 87 |
| 16 | IRMOF-74(II) | DPE | 120 | 16 | 9 | | | 75 | 78 |
| 17 | Ti@IRMOF-74(II) | DPE | 120 | 16 | 20 | | | 77 | 80 |
| 18 | Ni@IRMOF-74(II) | DPE | 120 | 16 | 34 | | | 85 | 87 |
| 19 | Ni@IRMOF-74(II) | PPE | 90 | 16 | 51 | 86 | | | 92 |
| 20 | Ni@IRMOF-74(II) | PPE | 100 | 16 | 56 | 76 | | | 79 |
| 21 | Ni@IRMOF-74(II) | PPE | 110 | 16 | 67 | 83 | | | 82 |
| 22 | Ni@IRMOF-74(II) | PPE | 120 | 1 | 39 | 86 | | | 91 |
| 23 | Ni@IRMOF-74(II) | PPE | 120 | 2 | 47 | 92 | | | 95 |
| 24 | Ni@IRMOF-74(II) | PPE | 120 | 4 | 56 | 93 | | | 97 |
| 25 | Raney Ni | PPE | 120 | 16 | 76 | 81 | | | 75 |
| 26 | $TiCl_3$ | PPE | 120 | 16 | 39 | 74 | | | 73 |

Experiments using pure IRMOF-74(I,II) catalysts revealed that all three ethers react with $H_2$ to generate small amounts of phenol and the corresponding aromatic hydrocarbon (FIG. 6). In all cases, higher conversions were obtained using the IRMOF-74(II) catalyst. The difference can be quite substantial. For example, the conversion of PPE increased from 12% to 39% by using IRMOF-74(II) as the catalyst instead of IRMOF-74(I) (Table 4). Optimized geometries computed using density functional theory (DFT) indicate that all three substrates will fit within the pores of either MOF (see Example 4 herein, as well as FIG. 13), suggesting that other factors, such as access to the OMS, the transition state geometry, or the reactant and/or product diffusion rates within the pore, may be responsible for this trend.

Figure 3A:
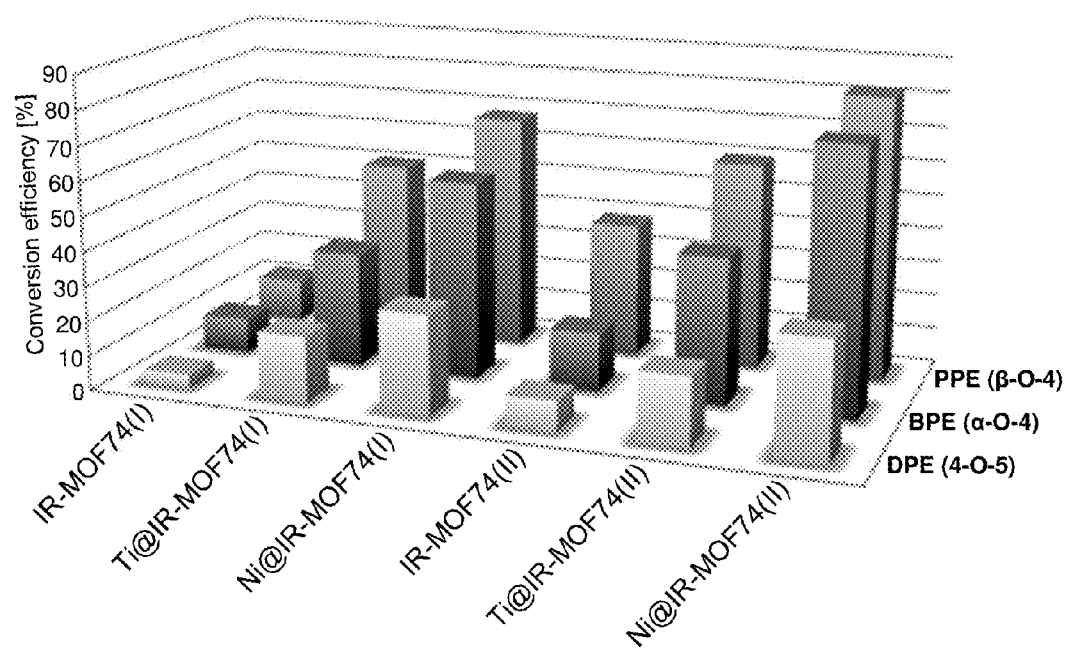
FIG. 3A-3B shows characterization of various MOF-based catalysts. Provided is (A) a graph showing conversion efficiencies of the substrates into the corresponding hydrocarbon and phenol at 120° C. under 10 bar hydrogen in the presence of Ni@IRMOF-74(II). Also provided is (B) powder XRD patterns of the as-synthesized, infiltrated, and cycled IRMOF-74(I) (left) and IRMOF-74(II) (right) catalysts.
Figure 8:
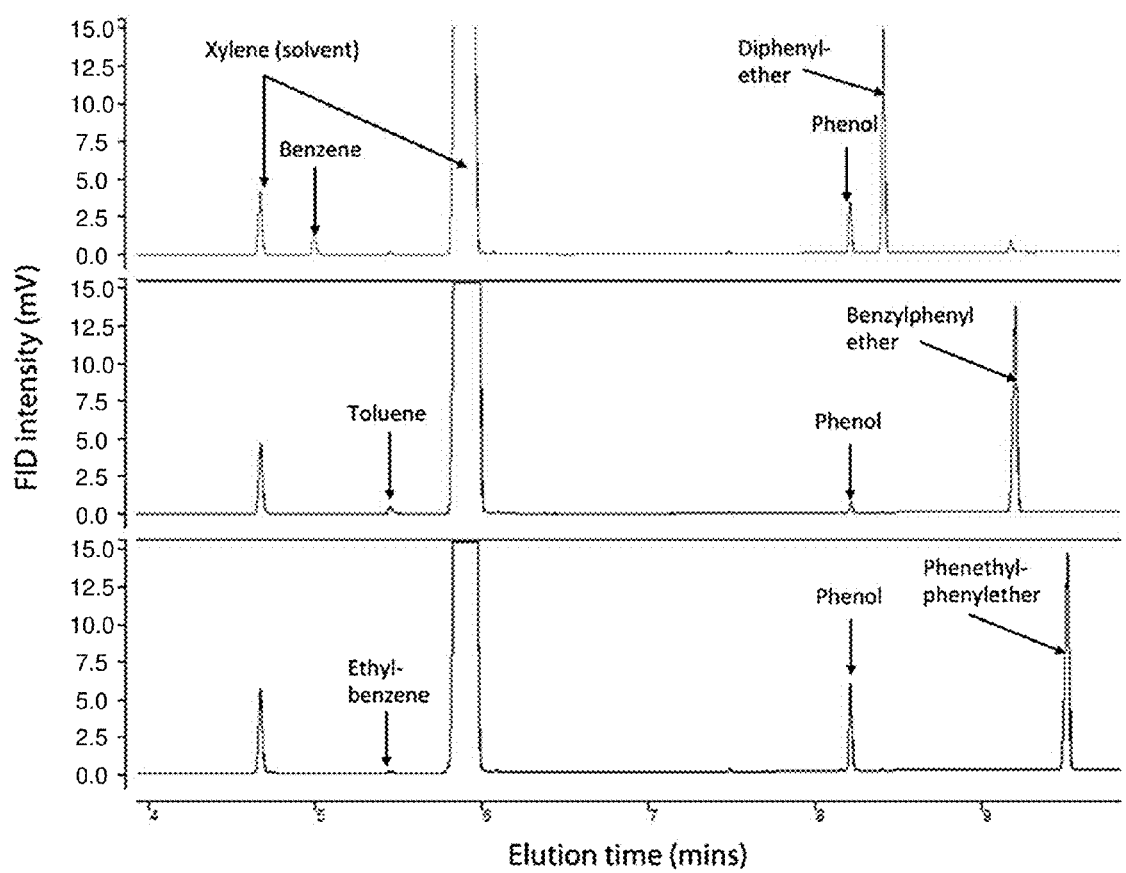
FIG. 8 shows gas chromatograms showing partial conversion of the substrates into the corresponding hydrocarbon and phenol at 120° C. under 10 bar hydrogen in the presence of Ni@IRMOF-74(II).

Performing the hydrogenolysis reactions in the presence of the TiCl, and Ni-infiltrated MOF catalysts leads to a significant increase in conversion efficiency (Table 4). GCMS analysis (FIG. 8) and $^1$H NMR analysis of the reaction products of all three substrate molecules clearly indicated new peaks corresponding to the monomeric products (compounds 1-4 in FIG. 6). The conversions obtained using both MOFs follow the trend PPE>BPE>DPE (FIG. 3A).

Table 5 shows the catalytic effect of Ni@IRMOF-74(I) upon cycling (cycles 1 through 5 are shown here; cycle 1 is entry no. 3 in Table 4), as well as results of tests in the absence of catalyst for all three substrates (1=ethylbenzene, 2=toluene, 3=benzene, 4=phenol).

TABLE 5

Cycling of MOF-based catalysts

| No. | Catalyst | Cycle | Substrate | T [° C.] | t [h] | Conv. [%] | Selectivity 1 | 2 | 3 | 4 |
|---|---|---|---|---|---|---|---|---|---|---|
| 3 | Ni@IRM0E-74(I) | 1 | PPE | 120 | 16 | 68 | 91 | | | 94 |
| 27 | Ni@IRMOF-74(I) | 2 | PPE | 120 | 16 | 69 | 93 | | | 95 |
| 28 | Ni@IRMOF-74(I) | 3 | PPE | 120 | 16 | 68 | 92 | | | 94 |
| 29 | Ni@IRMOF-74(I) | 4 | PPE | 120 | 16 | 65 | 90 | | | 93 |
| 30 | Ni@IRMOF-74(I) | 5 | PPE | 120 | 16 | 67 | 91 | | | 94 |
| 31 | No catalyst | NA | PPE | 120 | 16 | 0 | 0 | | | 0 |
| 32 | No catalyst | NA | BPE | 120 | 16 | 0 | | 0 | | 0 |
| 33 | No catalyst | NA | DPE | 120 | 16 | 0 | 0 | | | 0 |

In all cases (with or without $TiCl_x$ or Ni dopants), it is clear that the MOF-based catalysts facilitated the reaction; no substrate conversion occurred in the absence of the MOF catalyst (Table 5). When compared to commercial Raney Ni and $TiCl_3$ (entry nos. 25 and 26 in Table 4), the Ni@IRMOF and Ti@IRMOF catalysts displayed similar conversion efficiency, but significantly better selectivity. In addition, the products of the reactions catalyzed by Ni Raney included substantial quantities of cyclohexanol, whereas no products of ring hydrogenation or ring opening were detected in any of the reactions catalyzed by the MOFs.

PXRD data (FIG. 3B) indicate that the MOF structure was unchanged by the hydrogenolysis reaction. Moreover, elemental analysis of the supernatant following the reaction yielded no evidence of Mg, Ti, or Ni, confirming that the MOF itself is the active catalyst and not a solubilized metal component. Finally, repeated cycling of the catalysts did not affect their performance; for example, the recovered Ni@IRMOF-74(I) catalyst was reused for up to five tests without any significant loss in catalytic activity (Table 5, entry no. 30).

Figure 3B:
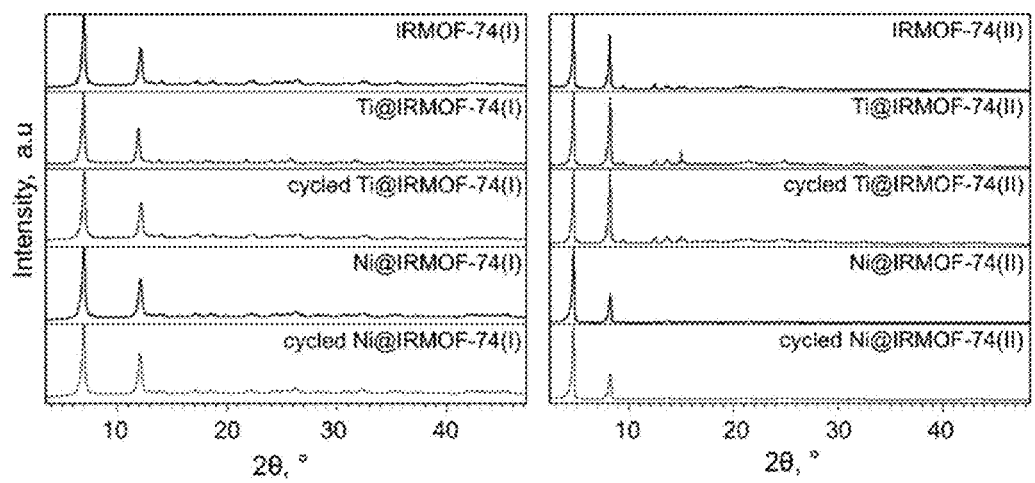

Powder XRD indicated that both IRMOF-74(I) and IRMOF-74(II) showed no signs of structural degradation or loss of crystallinity upon infiltration with guest species or after catalytic tests (FIG. 3B). The metal loadings, determined by elemental analysis, were 1.52 wt % Ti and 2.91 wt % Ni in IRMOF-74(I); and 1.75 wt % Ti and 3.07 wt % Ni in IRMOF-74(II). The Ti:Cl ratio in the titanium-infiltrated samples annealed under hydrogen was close to 1:3, suggesting that $Ti^{3+}$ species are present in the final product.

Figure 4:
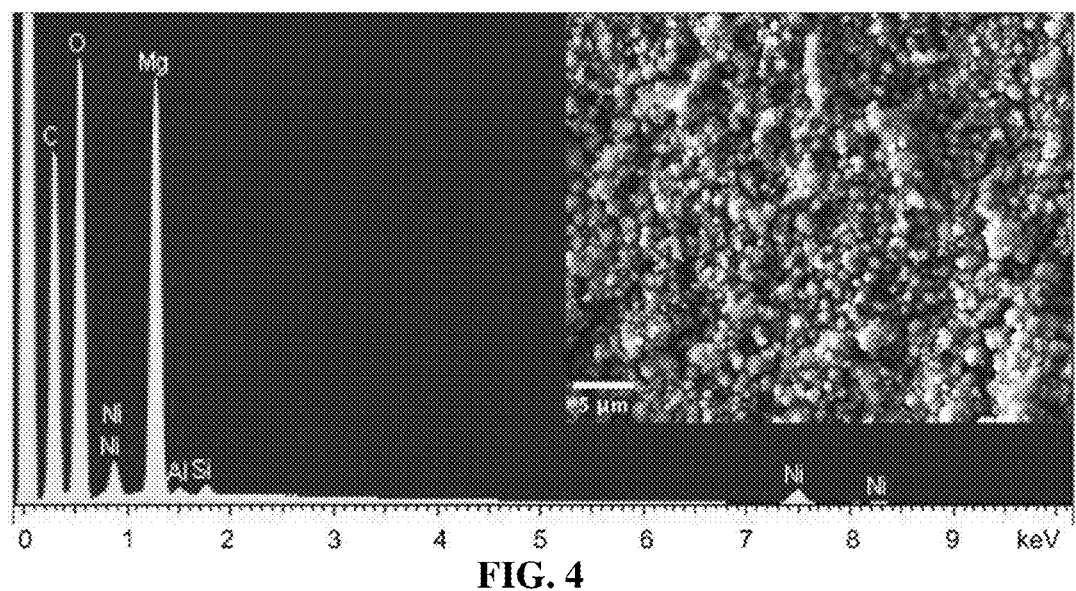
FIG. 4 shows an EDS spectrum of Ni@IRMOF-74(I), and the inset shows a representative SEM image of the as-synthesized catalyst sample. The small aluminum and silicon peaks are from the sample holder.
Figure 5A:
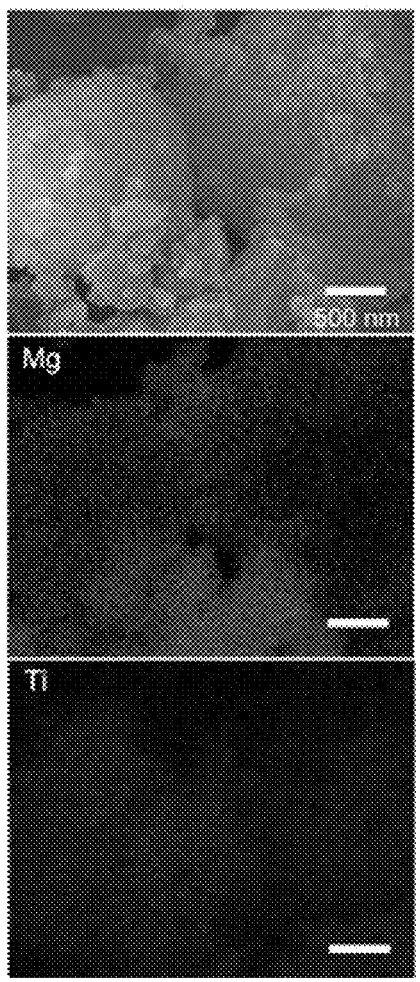
FIG. 5A-5D shows chemical and structural analysis of Ti- and Ni-doped IRMOF-74(I). Provided are (A) an SEM image and EDS maps (Mg or Ti) for Ti@IRMOF-74(I); (B) an SEM image and EDS maps (Mg or Ni) for Ni@IRMOF-74(I); (C) XPS analysis for Ti@IRMOF-74(I); and (D) XPS analysis for Ni@IRMOF-74(I). The scale bar in all EDS maps is 500 nm.
Figure 5B:
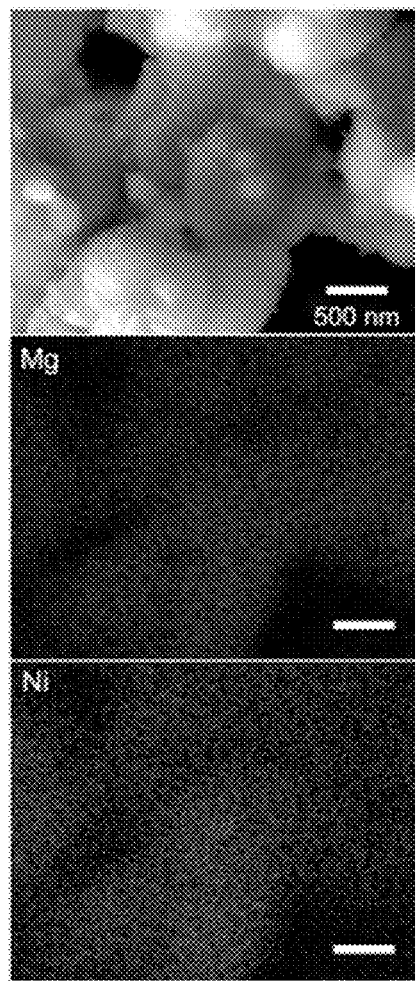

The metal distribution in the as-synthesized powders was determined through scanning electron microscopy (SEM) measurements using energy-dispersive spectroscopy (EDS). The elemental maps confirmed that both Ti and Ni species are present and were well dispersed within the MOF particles (FIG. 4 and FIG. 5A-5B). Because the penetration depth of 15 keV electrons used in EDS measurements is about 5 μm, this method probes the entire catalyst particle and not only its surface.

Figure 5C:
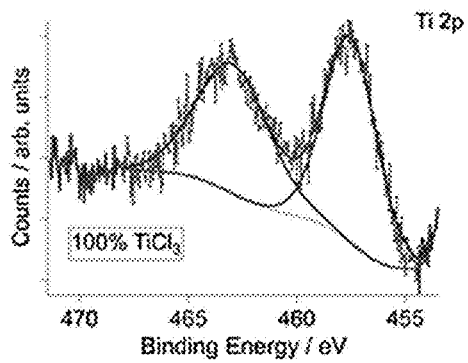
Figure 5D:
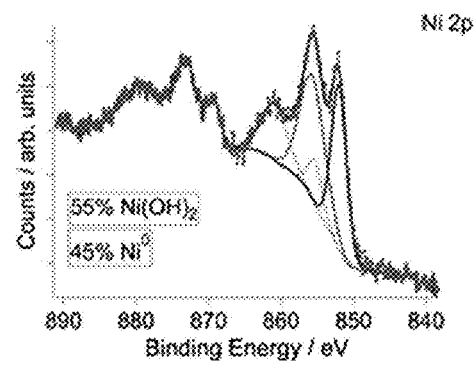

XPS measurements were also determined. These measurements indicated that the Ti(III) was present as $TiCl_3$, based on its characteristic peaks centered at 457.5 eV (Ti $2p_{3/2}$) and 463.0 eV (Ti $2p_{1/2}$) (FIG. 5C). In the case of Ni-doped samples, the species detected were 45% Ni0 and 55% $Ni(OH)_2$, as evidenced by the Ni $2p_{3/2}$ peaks located at 852.6 eV and 856.3 eV, respectively (FIG. 5D). The $Ni(OH)_2$ species likely result from the short exposure to air during the transfer of the sample into the XPS chamber (FIG. 4).

Nitrogen BET analysis indicated that the surface area of IRMOF-74(I) was reduced from 1627 $m^2/g$ for the activated material to 431 $m^2/g$ and 459 $m^2/g$ upon infiltration with Ti and Ni species, respectively. The surface area reduction was somewhat less for IRMOF-74(II), from 1736 $m^2/g$ for the activated IRMOF-74(II) to 672 $m^2/g$ and 591 $m^2/g$ for Ti@IRMOF-74(II) and Ni@IRMOF-74(II).

Mg-IRMOF-74 is a robust framework. For instance, TGA showed no decomposition below 350° C., and the MOF exhibited a surface area near the theoretical value after degassing under vacuum for 16 h at 225° C. (see, e.g., Caskey S R et al., "Dramatic tuning of carbon dioxide uptake via metal substitution in a coordination polymer with cylindrical pores," *J. Am Chem. Soc.* 2008; 130:10870-1; and Perry J J et al., "Noble gas adsorption in metal-organic frameworks containing open metal sites," *J. Phys. Chem. C* 2014; 118:11685-98). Thus, we believe that partial blockage of the 1D channels by guest species is the likely cause of the decreased surface area. Some pore collapse leading to amorphous domains undetectable by XRD cannot be fully ruled out, but if this occurs, these regions would most likely be inaccessible to guest molecules. The fact that the BET data showed the accessible pore volume remains after infiltration with Ti and Ni and that, in all cases, conversions were higher for the larger-pore IRMOF-74(II), points to reactions occurring within the MOF pores and not processes on the MOF surface.

The activity of the catalysts followed the trend of Ni@IRMOF-74>Ti@IRMOE-74>IRMOF-74, regardless of substrate, with the highest conversions obtained for the β-O-4 and α-O-4 linkages (82% and 76%, respectively) using Ni@IRMOF-74(II). More remarkably, all three catalysts displayed very good selectivity for hydrogenolysis versus hydrogenation, with selectivity toward ethylbenzene and phenol formation from PPE as high as 98%.

Figure 10:
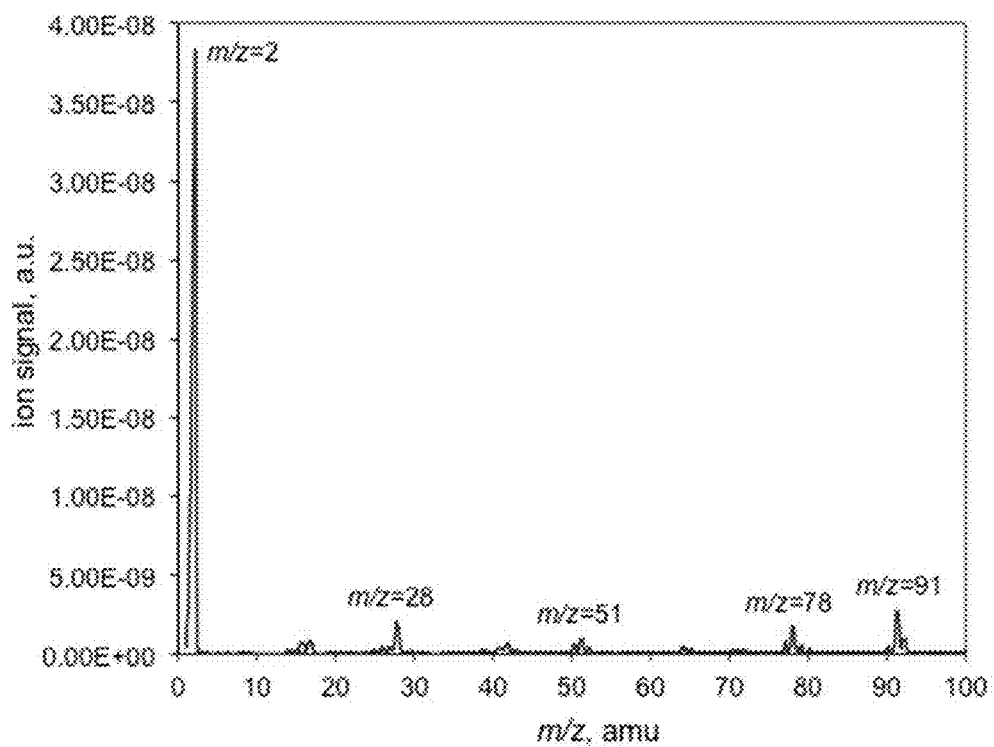
FIG. 10 shows residual gas analysis of the volatiles from the reaction in entry no. 6 in Table 4. The most significant feature at m/z=2 corresponds to hydrogen; and the species at m/z=78 and 91 correspond to fragments of aromatic hydrocarbons ($C_6H_6$ and $C_7H_8$) from the solvent and/or from reaction products.

Based on the stoichiometry of the reactions in FIG. 6, equal amounts of the two products should be obtained. We found that slightly lower amounts of compounds 1, 2, or 3 were obtained relative to phenol (compound 4, see Table 4). Without wishing to be limited by theory, this is likely due to the higher volatility of the compounds, leading to finite concentrations in the head space above the reaction that are not fully recovered when the hydrogen pressure is released. The residual gas analysis (RGA) measurements of the volatiles present in the reaction vessel indicate that, in addition to hydrogen (m/z=2), fragments of aromatic hydrocarbons (m/z=78, 91) (FIG. 10) from the solvent and/or reaction products are present as well.

That substrate confinement within the MOF pore plays a key role in establishing the efficiency and selectivity of these catalysts is supported by DFT calculations, which indicated that the OMS in the IRMOF-74 pores bind and orient the substrate within the pore. We used a cluster model (FIG. 11A-11C, FIG. 12A-12B, and FIG. 13) including four five-coordinate $Mg^{2+}$ ions, each connected to five oxygen donor atoms, approximating one wall of the hexagonal pore.

Computed binding energies (see Example 4 herein) indicated that all three substrates interact strongly with the cluster, even in the presence of the p-xylene solvent (Table 2, above; and Table 6, below).

TABLE 6

Computed ΔH° and ΔG° upon hydrogenolysis at 393K

| Substate | ΔH°$_B$ [kJ/mol] | | ΔG° [kJ/mol]* | |
| --- | --- | --- | --- | --- |
| | no solvent | with solvent | in gas phase | on MOF cluster |
| PPE | 135.1 | 81.9 | −103.5 | −142.3 |
| BPE | 124.5 | 75.2 | −106.6 | −129.1 |
| DPE | 44.9 | 37.2 | −80.3 | −81.8 |

*Substrate (or test compound) + H$_2$ → hydrocarbon + PhOH

These energies follow the trend PPE>BPE>DPE (Table 6), consistent with the experimental conversions. The involvement of the OMS is indicated by the observation that, for all three substrates, the relaxed cluster-substrate geometries position one of the substrate aromatic rings directly over a Mg$^{2+}$ ion (shown in FIG. 12A for PPE and FIG. 12B for PPE, BPE, and DPE).

Global charge transfer analysis (e.g., as described in Park Y K et al., *Chem. Commun.* 2010; 46:3086-88) indicates that in the MOF-substrate complex (Table 3, above), there is charge transfer from the model compound to the MOF, with the MOF acting as an electron acceptor and the aromatic ether molecules as electron donors. In addition, the computed free energies of hydrogenolysis (ΔG°) on the cluster are more negative than the purely gas-phase reaction (Table 6).

Examination of the predicted binding energies ΔH°$_B$ for the reactants and products chemisorbed to the cluster (or node) indicates that, in addition to orienting the substrate, the cluster may facilitate the reaction by stabilizing the products relative to the reactants; product binding energies are higher than those of the reactants (Table 2, above). Note that ΔG° (gas phase) represents the overall thermodynamic change for the hydrogenolysis reaction, whether or not the cluster is present.

Significantly, ΔH°$_B$ was considerably stronger and ΔG° was more negative for PPE and BPE than for DPE. Moreover, the interaction of DPE with the cluster had very little effect on the predicted ΔG° (−81.8 kJ/mol on the cluster versus −80.3 kJ/mol in the gas phase). These results are consistent with the experiments, which showed much higher conversions for PPE and BPE compared to DPE for all catalysts and conditions tested. We also note that the MOF OMS may play a role in activating or at least orienting H$_2$ in the pores; it is established by both neutron scattering studies and DFT calculations that the Mg$^{2+}$ OMS in Mg-IRMOF-74(I) are the strongest H$_2$ binding sites (see, e.g., Sumida K et al., "Hydrogen storage properties and neutron scattering studies of Mg$_2$(dobdc)—a metal-organic framework with open Mg$^{2+}$ adsorption sites," *Chem. Commun.* 2011; 47:1157-9; and Lee K et al., "Small-molecule adsorption in open-site metal-organic frameworks: a systematic density functional theory study for rational design," *Chem. Mater.* 2015; 27:668-78).

Clearly, the Ti and Ni dopants have an important, but different role from the MOF itself, one that is not directly addressed by our DFT calculations. However, a reasonable, non-limiting hypothesis is that the transition metal species inside the MOF pores activate dihydrogen molecules more efficiently than the pure MOFs, thereby reducing the activation energy of the hydrogenolysis reaction and generating higher concentrations of reactive H-species. Both Ti and Ni are well-known to activate the dihydrogen molecule (see, e.g., Saillard J Y et al., "Carbon-hydrogen and hydrogen-hydrogen activation in transition metal complexes and on surfaces," *J. Am. Chem. Soc.* 1984; 106:2006-26); and it is likely that they perform a similar role here. Our hypothesis suggests an additional, synergistic role for the MOF, namely, to increase the local concentration of active hydrogen, thereby accelerating the reaction. This is consistent with our prior study of Ti-doped Mg-IRMOF-74(I), which showed that the reversibility of NaAlH$_4$ decomposition in the pores is dramatically increased by the presence of the dopant.

In summary, Mg-IRMOF-74(I) and Mg-IRMOF-74(II) selectively catalyzed C—O aryl-ether bond cleavage, which is a new reaction category for MOFs. These results indicate that the MOF itself actively participates in the reaction, most likely through the interaction of the OMS with the substrate. Substrate conversion was enhanced by confinement of transition metal dopants within the MOF pores; additional mechanistic studies may be conducted to further determine the extent to which these effects are synergistic. Although the observed catalytic activity is slightly lower compared to the best-known C—O hydrogenolysis catalysts (see, e.g., Molinari V et al., *J. Am. Chem. Soc.* 2014; 136(5):1758-61; Wang X et al., *Chem Sus Chem* 2012; 5:1455-66; Sergeev A G et al., *J. Am. Chem. Soc.* 2012; 134:20226-9; and Sergeev A G et al., "Selective, nickel-catalyzed hydrogenolysis of aryl ethers," *Science* 2011; 332:439-43), a significant advantage of these MOF-based catalysts is that their activity is achieved without the addition of a base, such as NaOtBu (see, e.g., Sergeev A G et al., *J. Am. Chem. Soc.* 2012; 134:20226-9; and Sergeev A G et al., *Science* 2011; 332: 439-43).

Interestingly, Ni@IRMOF-74 had higher reactivity with PPE than DPE, whereas the ligand-less Ni catalyst reacted with these at comparable rates, suggesting the possibility of selective β-O-4 hydrogenolysis using the MOF. The Ni@IRMOF-74 catalysts also exhibited higher stability when recycled than Ni NPs stabilized on MIL-120, which exhibit consistent degradation of activity with reuse (see, e.g., Gascon J et al., *ACS Catal.* 2014; 4:361-78; and Wan Y et al., "Ni/MIL-120: An efficient metal-organic framework catalyst for hydrogenation of benzene to cyclohexane," *Microporous Mesoporous Mater.* 2013; 171:9-13).

Finally, in a few limited tests in which we suspended these catalysts in an ionic liquid (see Example 3 herein), no structural degradation or dissolution was observed after 16 h, indicating that these MOFs are compatible with some novel biomass pretreatment methods under development (see, e.g., Tadesse H et al., "Advances on biomass pretreatment using ionic liquids: an overview," *Energy Environ. Sci.* 2011; 4:3913-29).

Other Embodiments

All publications, patents, and patent applications, including U.S. Provisional Application No. 62/101,303, filed Jan. 8, 2015, mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method of cleaving a bond in a test compound comprising:
    exposing the test compound to a metal-organic framework in the presence of a hydrogen source, wherein the test compound comprises a carbon-oxygen bond,
    thereby cleaving the carbon-oxygen bond.

2. The method of claim 1, wherein the carbon-oxygen bond is an ether bond or an aryl ether bond.

3. The method of claim 1, wherein the metal-organic framework comprises a dopant.

4. The method of claim 3, wherein the dopant comprises a nanoparticle.

5. The method of claim 3, wherein the dopant comprises a second metal selected from the group consisting of titanium, nickel, rhodium, ruthenium, rhenium, iridium, copper, iron, platinum, palladium, and a combination thereof.

6. The method of claim 1, wherein the metal-organic framework comprises a plurality of nodes, an organic linker connecting at least two of the plurality of nodes, and an optional dopant comprising a second metal; and optionally wherein at least one of the plurality of nodes comprises one or more open metal sites.

7. The method of claim 6, wherein at least one of the plurality of nodes comprises a metal atom or a cluster thereof including a plurality of metal atoms.

8. The method of claim 7, wherein the metal atom comprises a metal ion.

9. The method of claim 6, wherein at least one node comprises magnesium or an ionic form thereof, the dopant comprises nickel and/or titanium or an ionic form thereof, and the organic linker comprises an optionally substituted arylene.

10. The method of claim 1, wherein the metal-organic framework comprises a pore having a diameter that is at least two times larger than a dimension of the test compound.

11. The method of claim 1, wherein the test compound is an organic compound, an organic polymer, or a biomass component.

12. The method of claim 1, wherein the test compound comprises lignin, cellulose, hemicellulose, and/or a fragment thereof.

13. The method of claim 1, wherein cleaving the carbon-oxygen bond forms two or more resultant cleavage products; and wherein each of the test compound and cleavage products is, independently, an organic moiety.

14. The method of claim 1, wherein the exposing step is further conducted in the presence of an ionic liquid and/or without the presence of a base.

15. The method of claim 1, further comprising:
    separating the metal-organic framework from the reacted test compound; and
    reusing the metal-organic framework for a further reaction with another test compound.

16. A method comprising:
    providing a biomass component; and
    exposing the biomass component to a metal-organic framework in the presence of a hydrogen source, wherein the biomass component comprises a carbon-oxygen bond,
    thereby cleaving the carbon-oxygen bond present in the biomass component.

17. The method of claim 16, wherein carbon-oxygen bond is an ether bond or an aryl ether bond.

18. The method of claim 16, wherein the metal-organic framework comprises a plurality of nodes, an organic linker connecting at least two of the plurality of nodes, and an optional dopant comprising a second metal; and optionally wherein at least one of the plurality of nodes comprises an open metal site.

19. The method of claim 16, wherein the exposing step is further conducted in the presence of an ionic liquid.

* * * * *